United States Patent
O'Hare et al.

(10) Patent No.: US 9,884,925 B2
(45) Date of Patent: Feb. 6, 2018

(54) SILYL BIS(HEXAMETHYLINDENYL) COMPLEXES OF GROUP IVA METALS AS POLYMERIZATION CATALYSTS

(71) Applicants: OXFORD UNIVERSITY INNOVATION LIMITED, Botley Oxford (GB); SCG CHEMICALS CO., LTD., Bangsue Bangkok (TH)

(72) Inventors: Dermot O'Hare, Oxford (GB); Jean-Charles Buffet, Oxford (GB)

(73) Assignees: OXFORD UNIVERSITY INNOVATION LIMITED, Oxford (GB); SCG CHEMICALS CO., LTD., Bangsue Bangkok (TH)

( * ) Notice: Subject to any disclaimer, the term of this patent is extended or adjusted under 35 U.S.C. 154(b) by 0 days.

(21) Appl. No.: 15/295,611

(22) Filed: Oct. 17, 2016

(65) Prior Publication Data
US 2017/0029537 A1 Feb. 2, 2017

Related U.S. Application Data

(63) Continuation of application No. PCT/GB2015/051137, filed on Apr. 14, 2015.

(30) Foreign Application Priority Data

Apr. 17, 2014 (GB) .................. 1407000.7

(51) Int. Cl.
*C08F 10/02* (2006.01)
*C07F 17/00* (2006.01)
(Continued)

(52) U.S. Cl.
CPC .............. *C08F 10/02* (2013.01); *C07F 17/00* (2013.01); *B01J 31/2295* (2013.01);
(Continued)

(58) Field of Classification Search
None
See application file for complete search history.

(56) References Cited

U.S. PATENT DOCUMENTS 5,672,668 A 9/1997 Winter et al.
5,696,045 A 12/1997 Winter et al.
(Continued)

FOREIGN PATENT DOCUMENTS

CA 2133389 9/1994
CA 2133181 3/1995
(Continued)

OTHER PUBLICATIONS

PCT Search Report and Written Opinion for PCT/GB2015/051137, dated Jul. 16, 2015.
(Continued)

*Primary Examiner* — Catherine S Branch
(74) *Attorney, Agent, or Firm* — Barnes & Thornburg LLP

(57) ABSTRACT

Novel Si-bridged metallocene catalysts of formula I defined herein are disclosed, as well as their use in olefin polymerisation reactions.

(Continued)

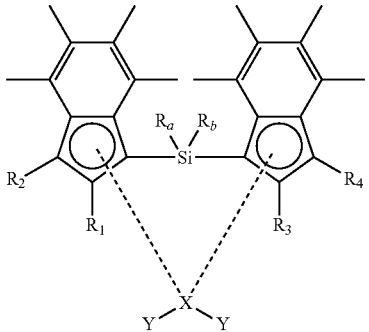

14 Claims, 22 Drawing Sheets

(51) Int. Cl.
  *C08F 110/02* (2006.01)
  *C08F 4/659* (2006.01)
  *B01J 31/22* (2006.01)

(52) U.S. Cl.
  CPC ........ *B01J 2531/46* (2013.01); *B01J 2531/48* (2013.01); *B01J 2531/49* (2013.01); *C08F 4/65912* (2013.01); *C08F 4/65916* (2013.01); *C08F 110/02* (2013.01); *C08F 2500/17* (2013.01); *C08F 2800/20* (2013.01)

(56) References Cited

U.S. PATENT DOCUMENTS

| | | | |
|---|---|---|---|
| 6,469,188 | B1 | 10/2002 | Miller et al. |
| 6,552,210 | B1 | 4/2003 | Gores et al. |
| 6,583,238 | B1 | 6/2003 | Gores et al. |
| 6,833,045 | B1 | 12/2004 | Tokita et al. |
| 8,980,781 | B2 | 3/2015 | O'Hare et al. |
| 2002/0039962 | A1 | 4/2002 | Schaverien et al. |
| 2003/0176275 | A1 | 9/2003 | Volker et al. |
| 2005/0182266 | A1 | 8/2005 | Schulte et al. |
| 2007/0105712 | A1 | 5/2007 | Panitzky et al. |
| 2007/0232483 | A1 | 10/2007 | Yang et al. |
| 2011/0136994 | A1 | 6/2011 | Ochi et al. |
| 2011/0282017 | A1 | 11/2011 | Kaji et al. |
| 2013/0059990 | A1 | 5/2013 | Kaji et al. |
| 2015/0057418 | A1 | 2/2015 | Kaji et al. |

FOREIGN PATENT DOCUMENTS

| | | |
|---|---|---|
| CN | 102294209 | 12/2011 |
| CN | 103525363 | 1/2014 |
| EP | 0645401 | 9/1994 |
| EP | 0646604 | 4/1995 |
| EP | 0704461 | 4/1996 |
| EP | 0707016 | 4/1996 |
| EP | 0646604 | 9/1997 |
| EP | 1055673 | 11/2000 |
| EP | 2570437 | 3/2013 |
| EP | 2706040 | 3/2014 |
| JP | 05125223 | 5/1993 |
| WO | WO1991/009881 | 7/1991 |
| WO | 1998043989 | 10/1998 |
| WO | 1998046616 | 10/1998 |
| WO | 2000026266 | 5/2000 |
| WO | WO2006/117285 | 11/2006 |
| WO | WO2009/077115 | 6/2009 |
| WO | WO2011/051705 | 5/2011 |
| WO | WO2012/048091 | 4/2012 |
| WO | WO2013/146337 | 10/2013 |
| WO | WO2014/051529 | 4/2014 |
| WO | WO2016/075486 | 5/2016 |
| WO | WO2016/075488 | 5/2016 |
| WO | WO2016/110698 | 7/2016 |
| WO | WO2016/110699 | 7/2016 |

OTHER PUBLICATIONS

Alias, F. M., et al., "Synthesis, Characterisation and Structure of a Strained Ring-Tilted Bis(Indenyl)Iron Complex," 1997, Journal of Organometallic Chemistry. vol. 528, Nr:1, pp. 47-58. (Abstract Only).

Silveira, et al. Metallocenes in ethylene polymerization studied by cyclic and differential pulse voltammetry, Appl. Catal., A, 2007, 344, 98.

Ransom et al. Synthesis. Characterization, and Polymerization Studies of Ethylenebis(hexamethylindenyl) Complexes of Zirconium and Hafnium, Organometallics, 2011, 30 800-814.

PCT Search Report/Written Opinion prepared for PCT/GB2010/0051791, dated Feb. 7, 2011.

GB Search Report prepared for GB0918736.0, dated Mar. 22, 2010.

Licht, E. H. et al., "Synthesis and characterization of bis(cyclopentadienyl)zirconium dichloride complexes with ω-fluorenylalkyl or silyl substituents and their application in catalytic ethylene polymerization," Journal of Molecular Catalysis A Chemica, 2000, 164, 9-23.

PCT International Search Report and Written Opinion prepared for PCT/GB2015/053456, dated Feb. 29, 2016, 13 pages.

PCT International Search Report and Written Opinion prepared for PCT/GB2016/050025, dated May 7, 2016, 12 pages.

PCT International Search Report and Written Opinion prepared for PCT/GB2015/053457, dated Feb. 5, 2016, 12 pages.

PCT International Search Report and Written Opinion prepared for PCT/GB2015/053459, dated Feb. 11, 2016, 9 pages.

Gauthier, W. J. et al., "Elastomeric poly(propylene): Influence of catalyst structure and polymerization conditions on polymer structure and properties," Macromolecules, 1995, 28, 3771-3778.

Buffet, J. et al, "Metallocene supported core@LDH catalysts for slurry phase ethylene polymerization," Chem. Communications, 2016, 52, 4076-4079.

PCT International Search Report and Written Opinion prepared for PCT/GB2016/050024, dated Apr. 26, 2016, 10 pages.

Chen, C. et al, "Tuneable ultra high specific surface area Mg/Al—Co 3 layered double hydroxides," Dalton Transactions: The International Journal for Inorganic, Organometallic And Bioinorganic Chemistry, 2015, 44, 16392-16398.

a)

b)

c)

a)

b)

c)

SILYL BIS(HEXAMETHYLINDENYL) COMPLEXES OF GROUP IVA METALS AS POLYMERIZATION CATALYSTS

CROSS-REFERENCE TO RELATED APPLICATIONS

This application is a continuation of International Application No. PCT/GB2015/051137 filed Apr. 14, 2015, which claims priority to United Kingdom Patent Application Serial Number 1407000.7, filed Apr. 17, 2014, of which both of which are incorporated herein by reference in their entirety.

INTRODUCTION

The present invention relates to catalysts. More specifically, the present invention relates to particular metallocene catalysts, and the use of such catalysts in polyolefin polymerization reactions.

BACKGROUND OF THE INVENTION

It is well known that ethylene (and α-olefins in general) can be readily polymerized at low or medium pressures in the presence of certain transition metal catalysts. These catalysts are generally known as Ziegler-Natta type catalysts.

A particular group of these Ziegler-Natta type catalysts, which catalyse the polymerization of ethylene (and α-olefins in general), comprise an aluminoxane activator and a metallocene transition metal catalyst. Metallocenes comprise a metal bound between two $\eta^5$-cyclopentadienyl type ligands. Generally the $\eta^5$-cyclopentadienyl type ligands are selected from $\eta^5$-cyclopentadienyl, $\eta^5$-indenyl and $\eta^5$-fluorenyl.

It is also well known that these $\eta^5$-cyclopentadienyl type ligands can be modified in a myriad of ways. One particular modification involves the introduction of a linking group between the two cyclopentadienyl rings to form ansa-metallocenes.

Numerous ansa-metallocenes of transition metals are known in the art. However, there remains a need for improved ansa-metallocene catalysts for use in polyolefin polymerization reactions. In particular, there remains a need for new metallocene catalysts with high polymerization activities/efficiencies.

There is also a need for catalysts that can produce polyethylenes with particular characteristics. For example, catalysts capable of producing linear high density polyethylene (LHDPE) with a relatively narrow dispersion in polymer chain length are desirable.

WO2011/051705 discloses ansa-metallocene catalysts based on two $\eta^5$-indenyl ligands linked via an ethylene group.

There remains a need for ansa-metallocene catalysts having improved polymerization activity. Moreover, due to the high value that industry places on such materials, there is also a need for ansa-metallocene catalysts capable of polymerizing α-olefins to high molecular weights, without compromising polydispersity. It is even further desirable that such catalysts can be easily synthesized.

The present invention was devised with the foregoing in mind.

SUMMARY OF THE INVENTION

According to a first aspect of the present invention there is provided a compound of the formula I shown below:

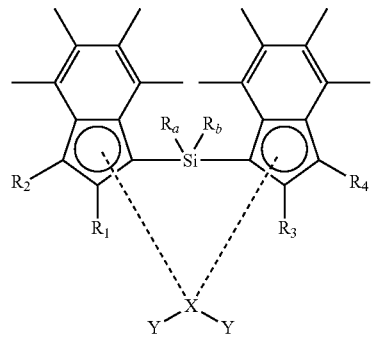

wherein:
$R_1$, $R_2$, $R_3$ and $R_4$ are each (1-3C)alkyl;
$R_a$ and $R_b$ are independently selected from (1-6C)alkyl, (1-6C)alkoxy, (2-6C)alkenyl, (2-6C)alkynyl, (1-6C)alkylamino, [(1-6C)alkyl]$_2$amino, aryl, halo, amino, nitro and cyano;
X is selected from zirconium, titanium or hafnium; and
each Y group is independently selected from halo, hydride, a phosphonated, sulfonated or borate anion, or a (1-6C)alkyl, (1-6C)alkoxy, aryl, aryl(1-4C)alkyl or aryloxy group which is optionally substituted with halo, nitro, amino, phenyl, (1-6C)alkoxy, or Si[(1-4C)alkyl]$_3$,
or, both Y groups are (1-3C)alkylene groups joined at their respective ends to a group Q, such that when taken with X and Q, the two Y groups form a 4, 5 or 6-membered ring;
wherein Q is a group Si($R_x$)($R_y$), wherein $R_x$ and $R_y$ are independently (1-4C)alkyl.

According to a second aspect of the present invention, there is provided a catalytic composition comprising a compound of formula I defined herein and a suitable activator as defined herein.

According to a third aspect of the present invention there is provided a use of a compound of formula I as defined herein as a polymerisation procatalyst in the polymerisation of a polyethylene According to a fourth aspect of the present invention there is provided a process for forming a polyethylene which comprises reacting olefin monomers in the presence of (i) a compound of formula I as defined herein, and (ii) a suitable activator.

DETAILED DESCRIPTION OF THE INVENTION

Definitions

Alkyl

The term "alkyl" as used herein includes reference to a straight or branched chain alkyl moieties, typically having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, an alkyl may have 1, 2, 3 or 4 carbon atoms.

Alkenyl

The term "alkenyl" as used herein include reference to straight or branched chain alkenyl moieties, typically having 1, 2, 3, 4, 5 or 6 carbon atoms. The term includes reference to alkenyl moieties containing 1, 2 or 3 carbon-carbon double bonds (C=C). This term includes reference to groups such as ethenyl (vinyl), propenyl (allyl), butenyl, pentenyl and hexenyl, as well as both the cis and trans isomers thereof.

Alkynyl

The term "alkynyl" as used herein include reference to straight or branched chain alkynyl moieties, typically having 1, 2, 3, 4, 5 or 6 carbon atoms. The term includes reference to alkynyl moieties containing 1, 2 or 3 carbon-carbon triple bonds (C≡C). This term includes reference to groups such as ethynyl, propynyl, butynyl, pentynyl and hexynyl.

Alkoxy

The term "alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Aryl

The term "aryl" as used herein includes reference to an aromatic ring system comprising 6, 7, 8, 9 or 10 ring carbon atoms. Aryl is often phenyl but may be a polycyclic ring system, having two or more rings, at least one of which is aromatic. This term includes reference to groups such as phenyl, naphthyl and the like.

Aryl(m-nC)alkyl

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

Halogen

The term "halogen" or "halo" as used herein includes reference to F, Cl, Br or I. In a particular, halogen may be F or Cl, of which Cl is more common.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled person.

Catalytic Compounds

As described hereinbefore, the present invention provides a compound of the formula I shown below:

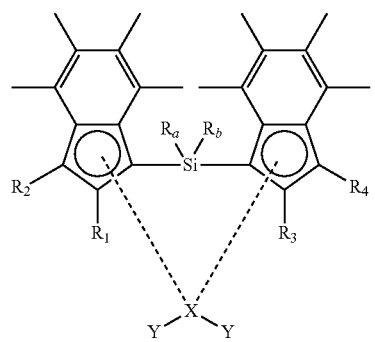

wherein:

$R_1$, $R_2$, $R_3$ and $R_4$ are each (1-3C)alkyl;

$R_a$ and $R_b$ are independently selected from (1-6C)alkyl, (1-6C)alkoxy, (2-6C)alkenyl, (2-6C)alkynyl, (1-6C)alkylamino, [(1-6C)alkyl]$_2$amino, aryl, halo, amino, nitro and cyano;

X is selected from zirconium, titanium or hafnium; and each Y group is selected from halo, hydride, a phosphonated, sulfonated or borate anion, or a (1-6C)alkyl, (1-6C)alkoxy, aryl, aryl(1-3C)alkyl or aryloxy group which is optionally substituted with halo, nitro, amino, phenyl, (1-6C)alkoxy, or Si[(1-4C)alkyl]$_3$, or, both Y groups are (1-3C)alkylene groups joined at their respective ends to a group Q, such that when taken with X and Q, the two Y groups form a 4, 5 or 6-membered ring; wherein Q is a group Si($R_x$)($R_y$), wherein $R_x$ and $R_y$ are independently (1-4C)alkyl.

It will be appreciated that the structural formula I presented above is intended to show the substituent groups in a clear manner. A more representative illustration of the spatial arrangement of the groups is shown in the alternative representation below:

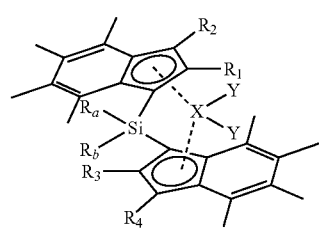

The compounds of the invention exhibit superior catalytic performance when compared with current metallocene compounds used in the polymerisation of α-olefins. In particular, when compared with current metallocene compounds used in the polymerisation of α-olefins, the compounds of the invention exhibit significantly increased catalytic activity. Moreover, polymers produced by α-olefin polymerization in the presence of compounds of the invention are typically of a higher molecular weight than polymers prepared using other catalysts, without an attendant increase in polydispersity. Such materials are highly valued by industry.

Suitably, when envisaged for use in the polymerisation of α-olefins, the compounds of the invention are immobilized on a suitable activator as defined herein. The compounds of the invention may be immobilized directly on the activator, or via a suitable linker. The compounds of the invention may be immobilized on the activator by one or more ionic or covalent interactions.

In an embodiment, $R_1$, $R_2$, $R_3$ and $R_4$ are each (1-2C) alkyl. Suitably, $R_1$, $R_2$, $R_3$ and $R_4$ are all methyl.

In another embodiment, X is zirconium or hafnium. Suitably, X is zirconium.

In another embodiment, $R_a$ and $R_b$ are each (1-6C)alkyl, (2-6C)alkenyl, (2-6C)alkynyl or phenyl. Suitably, $R_a$ and $R_b$ are each (1-4C)alkyl, (2-4C)alkenyl or (2-4C)alkynyl. Even more suitably, $R_a$ and $R_b$ are each independently selected from methyl, propyl and allyl. Most suitably, $R_a$ and $R_b$ are both methyl.

In another embodiment, Y is selected from halo or a (1-2C)alkyl group which is optionally substituted with halo, benzyl, phenyl, or $Si[(1-4C)alkyl]_3$,
or, both Y groups are methylene groups joined at their respective ends to a group Q, such that when taken with X and Q, the two Y groups form a 4-membered ring;
wherein Q is a group $Si(R_x)(R_y)$, wherein $R_x$ and $R_y$ are independently (1-2C)alkyl. Suitably, Y is halo. Most suitably, Y is chloro.

In an embodiment, the compound has the structural formula II shown below:

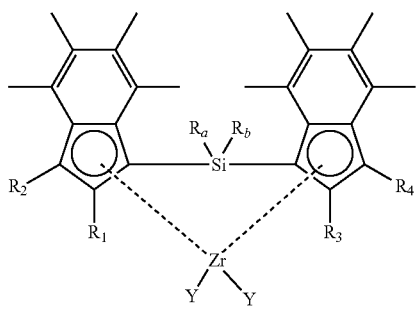

(II)

wherein
$R_1$, $R_2$, $R_3$ and $R_4$ are each (1-2C)alkyl;
$R_a$ and $R_b$ are independently selected from (1-6C)alkyl, (1-6C)alkoxy, (2-6C)alkenyl, (2-6C)alkynyl, (1-6C)alkylamino, $[(1-6C)alkyl]_2$amino, halo, amino, nitro and cyano; and
each Y group is independently halo.

In another embodiment, the compound has the structural formula III shown below:

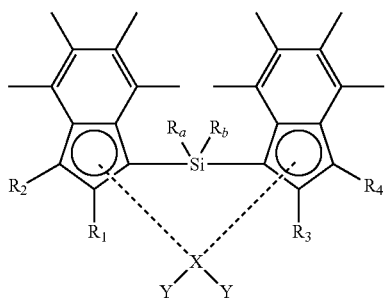

(III)

wherein
$R_1$, $R_2$, $R_3$ and $R_4$ are each (1-2C)alkyl;
$R_a$ and $R_b$ are independently selected from (1-6C)alkyl and (2-6C)alkenyl;
X is zirconium or hafnium; and
each Y group is independently halo.

In another embodiment, the compound has the structural formula IV shown below:

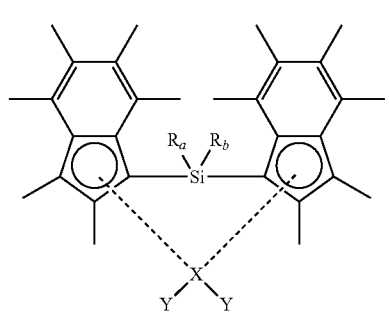

(IV)

wherein
$R_a$ and $R_b$ are independently selected from (1-6C)alkyl, (1-6C)alkoxy, (2-6C)alkenyl, (2-6C)alkynyl, (1-6C)alkylamino, $[(1-6C)alkyl]_2$amino, halo, amino, nitro and cyano;
X is selected from zirconium, titanium or hafnium; and
each Y group is selected from halo, hydride, a phosphonated or sulfonated anion, or a (1-6C)alkyl, (1-6C)alkoxy, aryl or aryloxy group which is optionally substituted with halo, nitro, amino, phenyl, (1-6C)alkoxy, or $Si[(1-4C)alkyl]_3$.

In another embodiment, the compound has the structural formula V shown below:

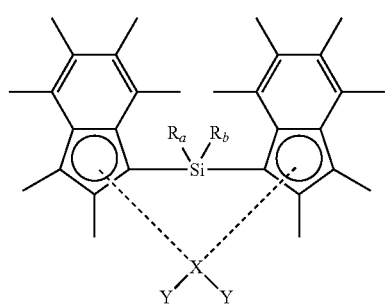

(V)

wherein
$R_a$ and $R_b$ are independently selected from (1-6C)alkyl and (2-6C)alkenyl;
X is zirconium or hafnium; and
each Y group is independently as defined hereinbefore.

In another embodiment, the compound has the structural formula VI shown below:

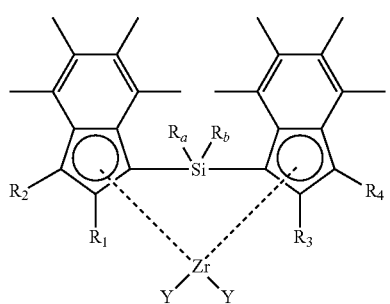

(VI)

wherein

R$_1$, R$_2$, R$_3$ and R$_4$ are each (1-2C)alkyl;

R$_a$ and R$_b$ are independently selected from (1-2C)alkyl and (2-6C)alkenyl; and each Y group is independently halo.

In another embodiment, the compound has the structural formula VII shown below:

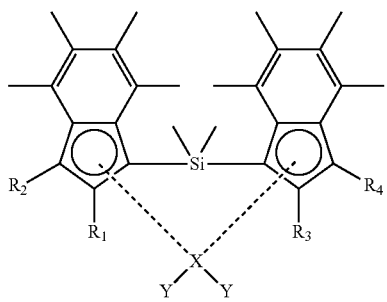

(VII)

wherein

R$_1$, R$_2$, R$_3$ and R$_4$ are each (1-2C)alkyl;

X is zirconium or hafnium; and each Y group is independently as defined hereinbefore.

In another embodiment, the compound has the structural formula VIII shown below:

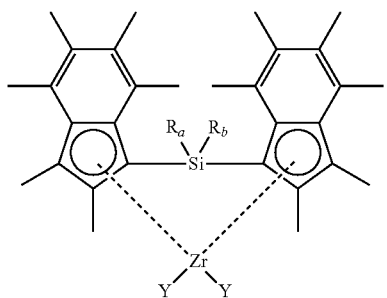

(VIII)

wherein

R$_a$ and R$_b$ are independently selected from methyl, propyl and allyl; and each Y group is independently halo.

The compounds of the present invention may be present in one or more isomeric forms. In particular, the compounds of the present invention may be present as meso or rac isomers, and the present invention includes both such isomeric forms. A person skilled in the art will appreciate that a mixture of isomers of the compound of the present invention may be used for catalysis applications, or the isomers may be separated and used individually (using techniques well known in the art, such as, for example, fractional crystallization).

Catalytic Compositions

As defined hereinbefore, the present invention provides a catalytic composition comprising a compound of formula I defined herein and a suitable activator as defined herein.

Suitably, the compound of formula I is immobilized on the activator. The compound of the invention may be immobilized directly on the activator, or via a suitable linker.

Any activator defined herein may be used. For example, the composition comprises a compound of formula I defined herein supported on a Solid MAO activator. Suitably, the Solid MAO activator is as described in US2013/0059990 and obtainable from Tosoh Finechem Corporation, Japan.

In an embodiment, the compound of the invention is immobilized on the activator by one or more ionic or covalent interactions.

Synthesis

The compounds of the present invention may be formed by any suitable process known in the art. Particular examples of processes for the preparing compounds of the present invention are set out in the accompanying examples.

Generally, the processes of preparing a compound of the present invention as defined herein comprises:

(i) reacting a compound of formula A:

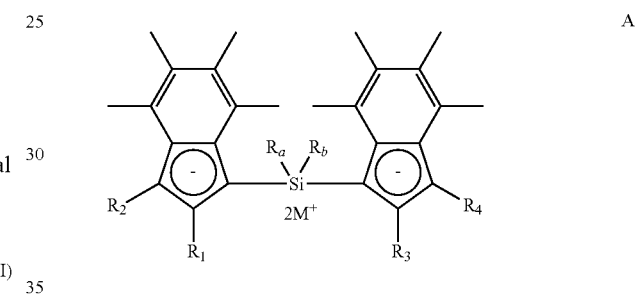

A (wherein R$_1$, R$_2$, R$_3$ and R$_4$ are each as defined hereinbefore and M is Li, Na or K) with a compound of the formula B:

X(Y')$_4$     B (wherein X is as defined hereinbefore and Y' is halo (particularly chloro or bromo)) in the presence of a suitable solvent to form a compound of formula Ia:

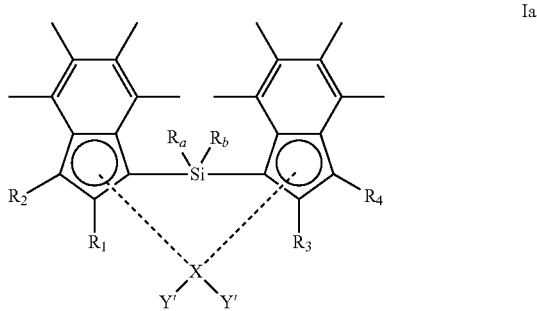

Ia and optionally thereafter:

(ii) reacting the compound of formula Ia above with MY" (wherein M is as defined above and Y" is a group Y as defined herein other than halo), in the presence of a suitable solvent to form the compound of the formula Ib shown below

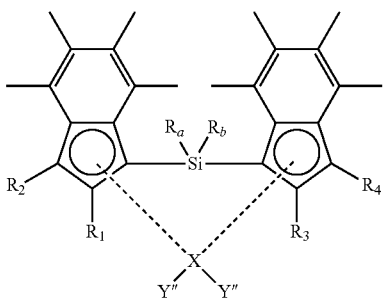

Ib

Suitably, M is Li in step (i) of the process defined above.

In an embodiment, the compound of formula B is provided as a solvate. In particular, the compound of formula B may be provided as $X(Y')_4 \cdot THF_p$, where p is an integer (e.g. 2).

Any suitable solvent may be used for step (i) of the process defined above. A particularly suitable solvent is toluene, benzene or THF.

If a compound of formula I in which Y is other than halo is required, then the compound of formula Ia above may be further reacted in the manner defined in step (ii) to provide a compound of formula Ib.

Any suitable solvent may be used for step (ii) of the process defined above. A suitable solvent may be, for example, diethyl ether, toluene, THF, dichloromethane, chloroform, hexane DMF, benzene etc.

A person of skill in the art will be able to select suitable reaction conditions (e.g. temperature, pressures, reaction times, agitation etc.) for such a synthesis.

Processes by which compounds of the formula A above can be prepared are well known art. For example, a process for the synthesis of a di-sodium ethylene-bis-hexamethyl-indenyl ligand of formula A is described in J. Organomet. Chem., 694, (2009), 1059-1068.

Compounds of formula A, in which $R_1$ and $R_3$, and $R_2$ and $R_4$ are the same, may generally be prepared by:
(i) Reacting, in a suitable solvent (such as tetrahydrofuran), two equivalents of a compound having formula D shown below

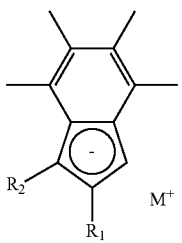

D (wherein M is lithium, sodium, or potassium; and $R_1$ and $R_2$ are as defined hereinbefore) with one equivalent of a compound having formula E shown below:

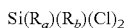    E (wherein $R_a$ and $R_b$ are as defined hereinbefore)

Compounds of formula D can be readily synthesized by techniques well known in the art.

When compared with ethylene-bridged ansa-metallocene catalysts, the Si-bridged compounds of the invention can be realised in fewer synthetic steps.

A person of skill in the art will be able to select suitable reaction conditions (e.g. temperature, pressures, reaction times, agitation etc.) for such a synthesis.

Applications

As previously indicated, the compounds of the present invention are extremely effective as catalysts in polyethylene polymerization reactions.

As discussed hereinbefore, the compounds of the invention exhibit superior catalytic performance when compared with current metallocene compounds used in the polymerisation of α-olefins. In particular, when compared with current metallocene compounds used in the polymerisation of α-olefins, the compounds of the invention exhibit significantly increased catalytic activity. Moreover, polymers produced by α-olefin polymerization in the presence of compounds of the invention are typically of a higher molecular weight than polymers prepared using other catalysts, without an attendant increase in polydispersity. Such materials are highly valued by industry.

Thus, the present invention also provides the use of a compound of formula I as defined herein as a polymerization catalyst, in particular a polyethylene polymerization catalyst.

In one embodiment, the polyethylene is made from polymerized ethene monomers.

In another embodiment, the polyethylene is made from polymerized ethene monomers comprising 1-10 wt % of (4-8C) α-olefin (by total weight of the monomers). Suitably, the (4-8C) α-olefin is 1-butene, 1-hexene, 1-octene, or a mixture thereof.

The present invention also provides a process for forming a polyolefin (e.g. a polyethylene) which comprises reacting olefin monomers in the presence of a compound of formula I as defined herein and a suitable activator.

In one embodiment, the process for forming a polyolefin proceeds via slurry polymerisation.

In another embodiment, the olefin monomers are ethene monomers.

In another embodiment, the olefin monomers are ethene monomers comprising 1-10 wt % of (4-8C) α-olefin (by total weight of the monomers). Suitably, the (4-8C) α-olefin is 1-butene, 1-hexene, 1-octene, or a mixture thereof.

Suitable activators are well known in the art and include, but are not limited to, aluminoxanes (e.g. methylaluminoxane (MAO)), triisobutylaluminium (TIBA) and triethylaluminium (TEA).

In a particular embodiment, the activator is provided as an activated support. Suitably, the activated support is insoluble under the polymerisation conditions. Suitable activated supports include methylaluminoxane activated silica ($SiO_2$), solid methylaluminoxane and methylaluminoxane activated AMO-MgAl layered double hydroxide (eg. $[Mg_{1-x}Al_x(OH)_2]^{x+}(A^{n-})_{x/n} \cdot y(H_2O) \cdot w(solvent)$ (0.1<x>0.9; A=anion eg. $CO_3^{2-}$, $OH^-$, $F^-$, $Cl^-$, $Br^-$, $I^-$, $SO_4^{2-}$, $NO_3^-$ and $PO_4^{3-}$), w is a number less than 1, y is 0 or a number greater than 0 which gives compounds optionally hydrated with a stoichiometric amount or a non-stoichiometric amount of water and/or an aqueous-miscible organic solvent (AMO-solvent), such as acetone.

In another embodiment, the activator is Solid MAO. Solid methyl aluminoxane (MAO) (often referred to as polymethylaluminoxane) is distinguished from other methyl aluminoxanes (MAOs) as it is insoluble in hydrocarbon solvents and so acts as a heterogeneous support system. Any suitable solid MAO support may be used.

In an embodiment, the solid MAO support is insoluble in toluene and hexane.

In another embodiment, the solid MAO support is in particulate form. Suitably, the particles of the solid MAO support are spherical, or substantially spherical, in shape.

In a particularly suitable embodiment, the solid MAO support is as described in US2013/0059990 and obtainable from Tosoh Finechem Corporation, Japan.

In another embodiment, the solid MAO support comprises additional compound selected from $M(C_6F_5)_3$, wherein M is aluminium or boron, or $M'R_2$, wherein M' is zirconium or magnesium and R is (1-10C)alkyl (e.g. methyl or octyl).

In another embodiment, the compound of formula I defined herein is immobilized on the activator. Suitably, the compound of formula I defined herein is immobilized on the activator (e.g. Solid MAO) by one or more ionic or covalent interactions.

In another embodiment, when the compound of formula I defined herein is immobilized on the activator, an additional activator. Suitable additional activators are well known in the art and include organo aluminium compounds (e.g. alkyl aluminium compounds). Particularly suitable additional activators include aluminoxanes (e.g. methylaluminoxane (MAO)), triisobutylaluminium (TIBA), diethylaluminium (DEAC) and triethylaluminium (TEA).

A person skilled in the art of olefin polymerization will be able to select suitable reaction conditions (e.g. temperature, pressures, reaction times etc.) for such a polymerization reaction. A person skilled in the art will also be able to manipulate the process parameters in order to produce a polyolefin having particular properties.

In a particular embodiment, the polyolefin is polyethylene.

EXAMPLES

Examples of the invention will now be described by reference to the accompanying figures, in which.

Figure 14:
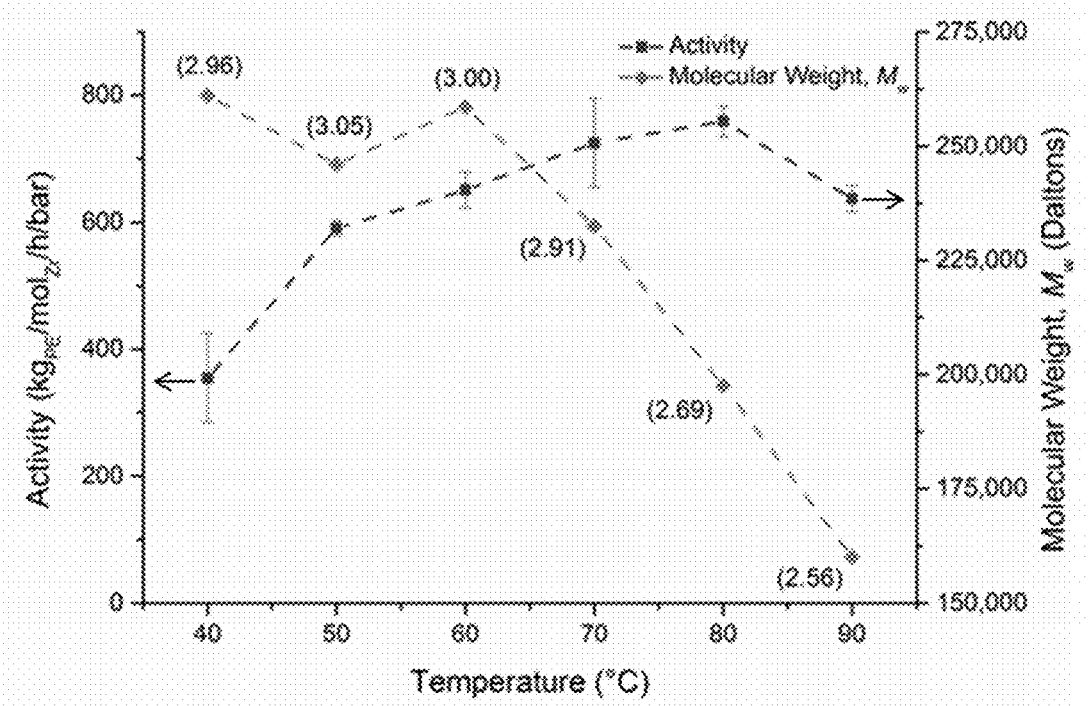

FIG. 14 shows a graph demonstrating the dependence of activity and M$_w$ for rac-(SBI*)ZrCl$_2$ on temperature. PDIs are given in parentheses. Supported on SSMAO (200:1 loading); TIBA co-catalyst; 2 bar ethylene; 10 mg catalyst; 50 ml hexane; 30 minutes.

Figure 15:
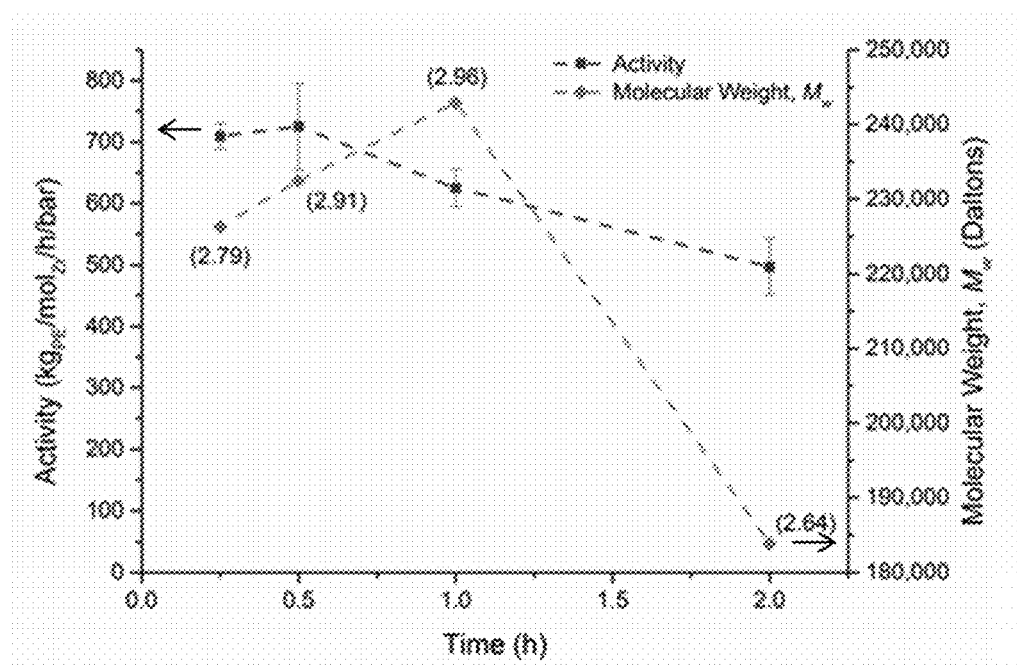

FIG. 15 shows a graph demonstrating the dependence of activity and M$_w$ for rac-(SBI*)ZrCl$_2$ on length of run. PDIs are given in parentheses. Supported on SSMAO (200:1 loading); TIBA co-catalyst; 70° C.; 2 bar ethylene; 10 mg catalyst; 50 ml hexane.

Figure 16:
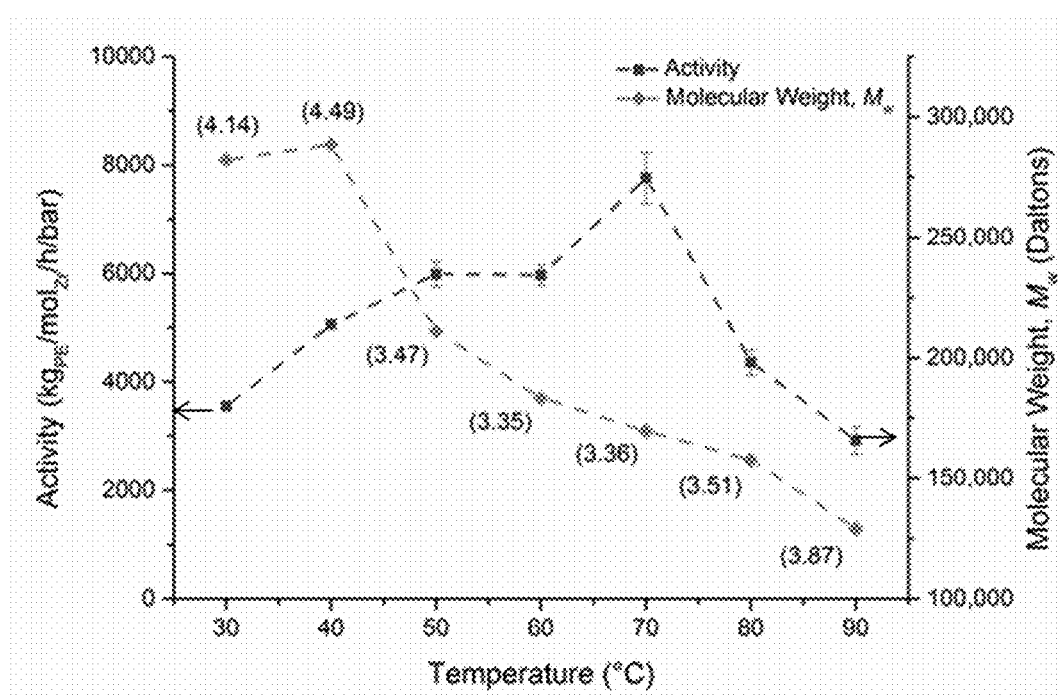

FIG. 16 shows a graph demonstrating the dependence of activity and M$_w$, for rac-(SBI*)ZrCl$_2$ on temperature. PDIs are given in parentheses. Supported on Solid MAO (300:1 loading); TIBA co-catalyst; 2 bar ethylene; 10 mg catalyst; 50 ml hexane; 30 minutes.

Figure 17:
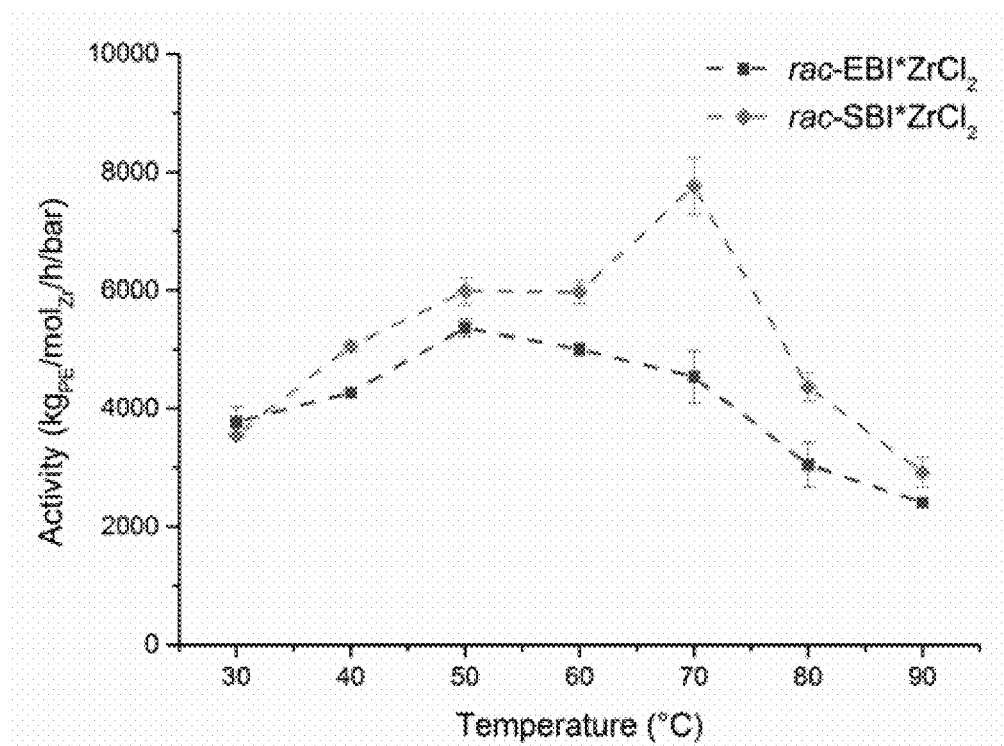

FIG. 17 shows a graph demonstrating the ethylene polymerisation activity dependence of rac-EBI*ZrCl$_2$ and rac-(SBI*)ZrCl$_2$ on temperature. Supported on Solid MAO (200:1 rac-EBI*ZrCl$_2$, 300:1 rac-SBI*ZrCl$_2$); TIBA co-catalyst; 2 bar ethylene; 10 mg catalyst; 50 ml hexane; 30 minutes.

Figure 18:
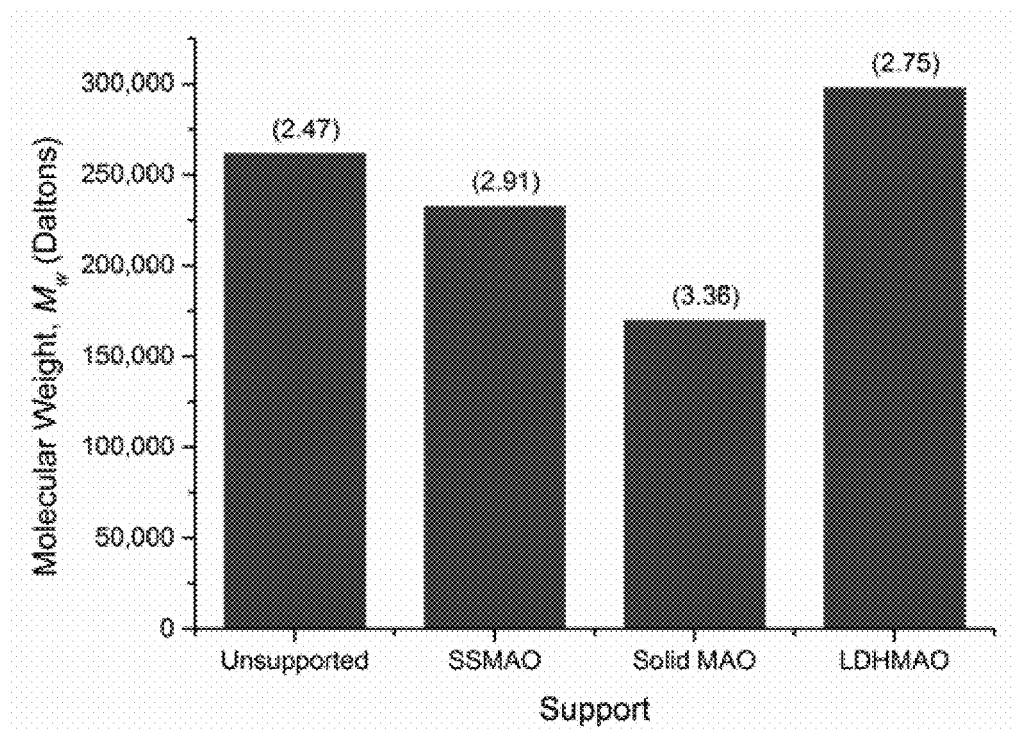

FIG. 18 shows a graph demonstrating the variation in molecular weight, M$_w$, of the polyethylene produced by rac-(SBI*)ZrCl$_2$ in solution and on three different supports. PDIs are given in parentheses. 70° C.; 2 bar ethylene; 0.2 mg catalyst (solution), 10 mg catalyst (slurry); 50 ml hexane; timed until cessation of stirring or 30 minutes, where possible.

Figure 19:
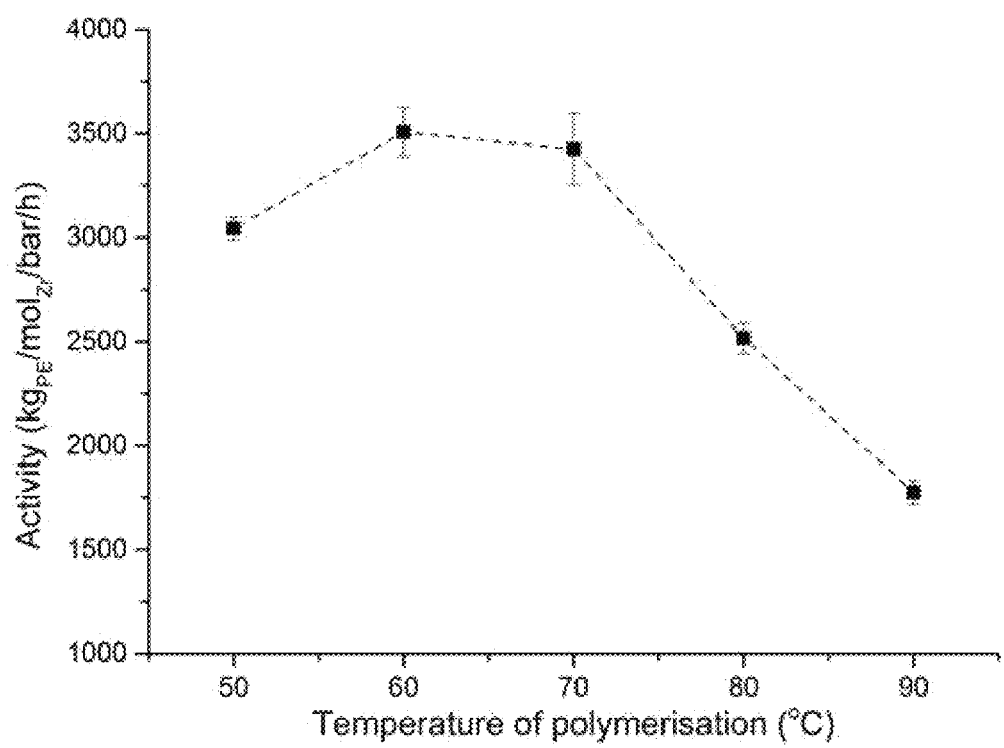

FIG. 19 shows a graph demonstrating the ethylene polymerisation activity dependence of rac-(SBI*$^{\eta3\text{-}ethyl}$)ZrCl$_2$ on temperature. Supported on Solid MAO (200:1); TIBA co-catalyst; 2 bar ethylene; 10 mg catalyst; 50 ml hexane; 30 minutes.

Figure 20:
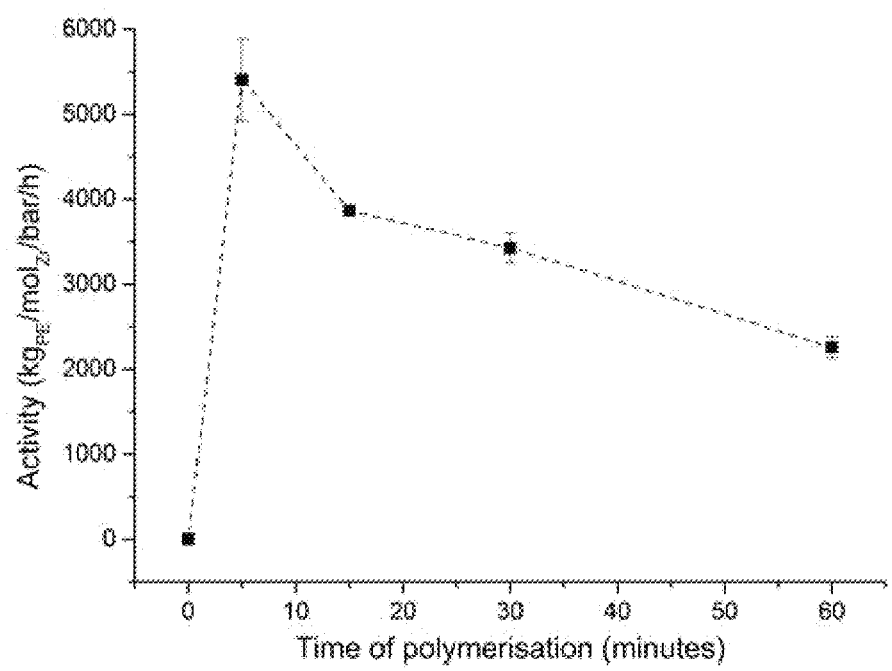

FIG. 20 shows a graph demonstrating the ethylene polymerisation activity dependence of rac-(SBI*$^{\eta3\text{-}ethyl}$)ZrCl$_2$ on time. Supported on Solid MAO (200:1); TIBA co-catalyst; 2 bar ethylene; 10 mg catalyst; 50 ml hexane; 30 minutes.

Figure 21:
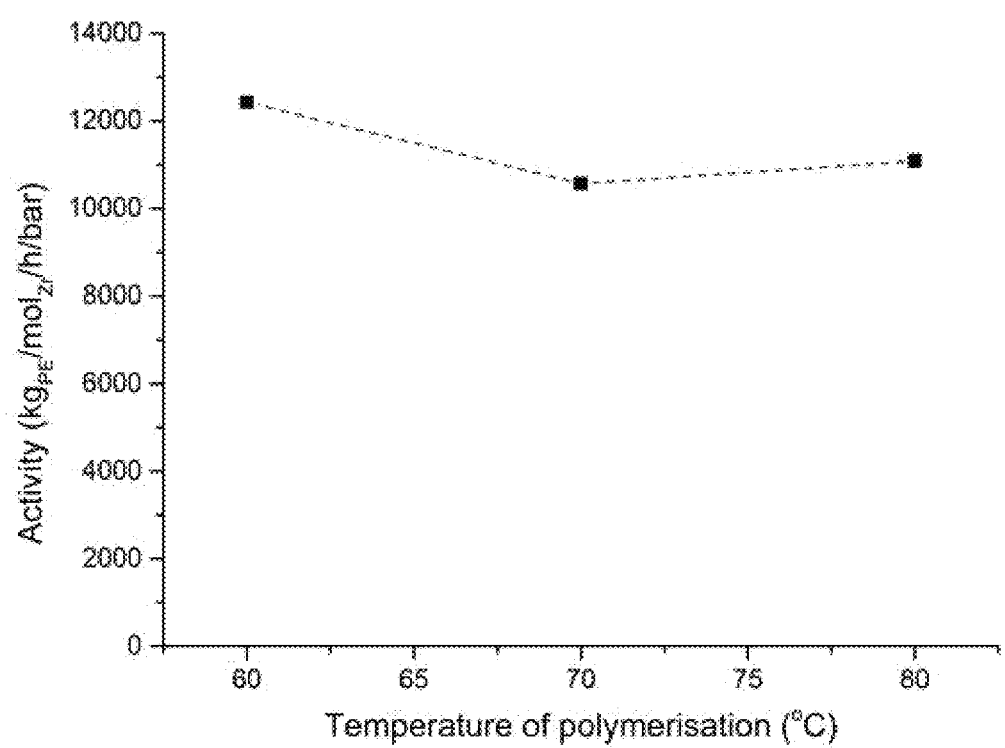

FIG. 21 shows a graph demonstrating the ethylene polymerisation activity dependence of rac-(SBI*$^{\eta3\text{-}ethyl}$)ZrCl$_2$ on temperature in solution. MAO co-catalyst; 2 bar ethylene; 0.5 mg complex; 50 ml hexane; 2 minutes.

Figure 22:
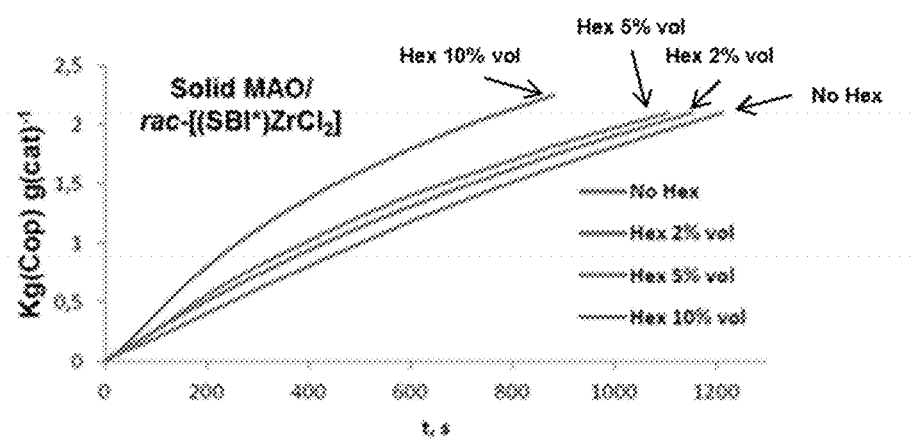

FIG. 22 shows a graph demonstrating the ethylene-1-hexene copolymerisation activity dependence of Solid MAO/rac-(SBI*)ZrCl$_2$ on time. TEA co-catalyst; 8 bar ethylene; 0.10 mg catalyst; 5 ml heptane; 70° C.

INTERMEDIATE 1

Synthesis of Si-Bridged Alkyl Indenyl Ligands ((SBI) Ligands)

The synthesis of silane proligands was achieved by reacting two equivalents of indenyl lithium, [(Ind$^\#$)Li], with one equivalent dichlorosilane at room temperature in tetrahydrofuran. After work-up, [(SBI*)H$_2$], [($^{Me,Propyl}$SBI*)H$_2$] and [($^{Me,Allyl}$SBI*)H$_2$], shown below, were obtained as colourless powders in high yield.

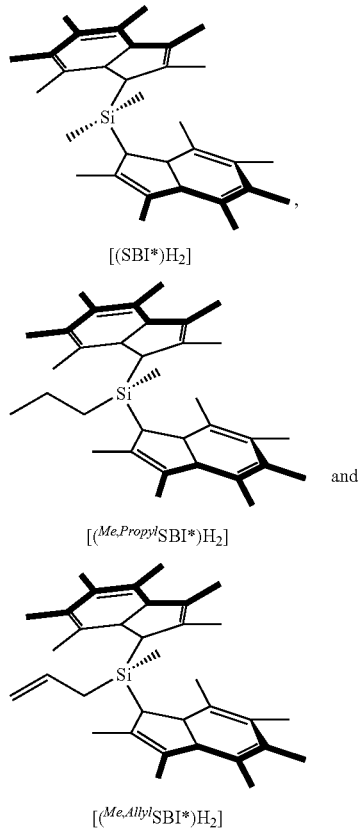

[(SBI*)H$_2$]

[($^{Me,Propyl}$SBI*)H$_2$] and

[($^{Me,Allyl}$SBI*)H$_2$]

Example 1

Synthesis of Si-Bridged Alkyl Indenyl Zirconocene Complexes

Synthesis of [(SBI*)ZrCl$_2$]

The synthesis of [(SBI*)ZrCl$_2$] was achieved by reacting [(SBI*)H$_2$] with two equivalents of n-butyllithium at room temperature. After work-up, [(SBI*)Li$_2$] was obtained as a yellow powder in quantitative yield.

In a Schlenk tube, 1.06 mmol stoichiometric reaction of 0.5 g of [(SBI*)Li$_2$] and 0.25 g of ZrCl$_4$ in benzene (50 mL) was stirred at room temperature for 2 hours. Then the red solution was filtered away from the colourless solid, LiCl, by-product, concentrated in vacuum to half and leaved standing over-night at room temperature. Orange crystals were formed, the solution was filtered away and the crystals were dried to afford rac-[(SBI*)ZrCl$_2$], shown below, as an orange solid in crystalline material yield.

Scheme 1: Synthesis of rac-[(SBI*)ZrCl$_2$]

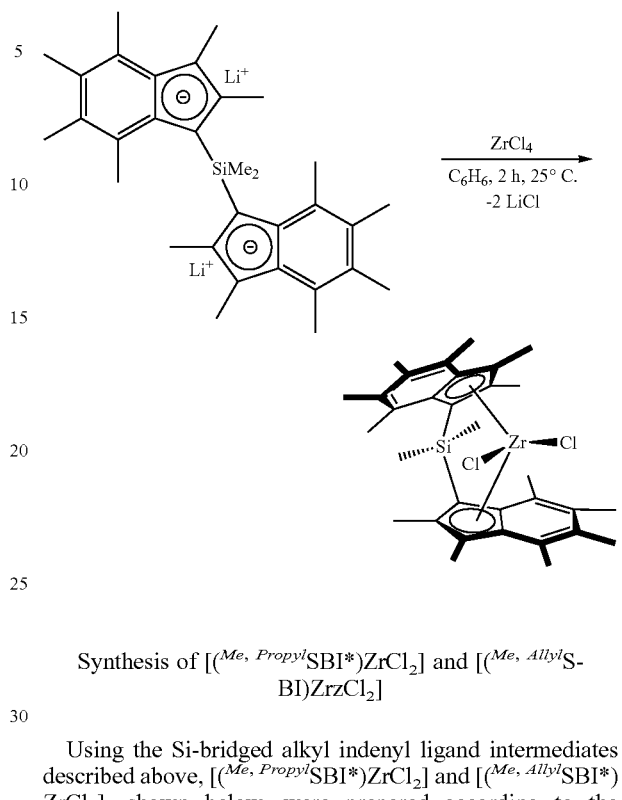

Synthesis of [($^{Me, Propyl}$SBI*)ZrCl$_2$] and [($^{Me, Allyl}$SBI)ZrzCl$_2$]

Using the Si-bridged alkyl indenyl ligand intermediates described above, [($^{Me, Propyl}$SBI*)ZrCl$_2$] and [($^{Me, Allyl}$SBI*)ZrCl$_2$], shown below, were prepared according to the method described in relation to [(SBI*)ZrCl$_2$] above.

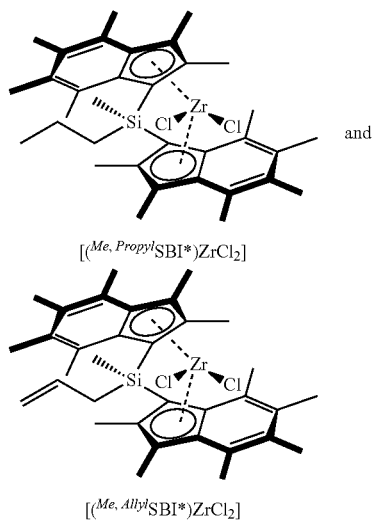

[($^{Me, Propyl}$SBI*)ZrCl$_2$] and

[($^{Me, Allyl}$SBI*)ZrCl$_2$]

Synthesis of dimethylsiliconbis[1(2,3,4,5,6,7-hexamethylindenyl)]zirconium dibenzyl, [(SBI*)Zr(CH$_2$Ph)$_2$]

Using the Si-bridged alkyl indenyl ligand intermediates described above, [(SBI*)Zr(CH$_2$Ph)$_2$], shown below, was prepared according to the method described in relation to [(SBI*)ZrCl$_2$] above.

Scheme 2: Synthesis of dimethylsiliconbis[1(2,3,4,5,6,7-hexamethylindenyl)]zirconium dibenzyl, [(SBI*)Zr(CH₂Ph)₂]

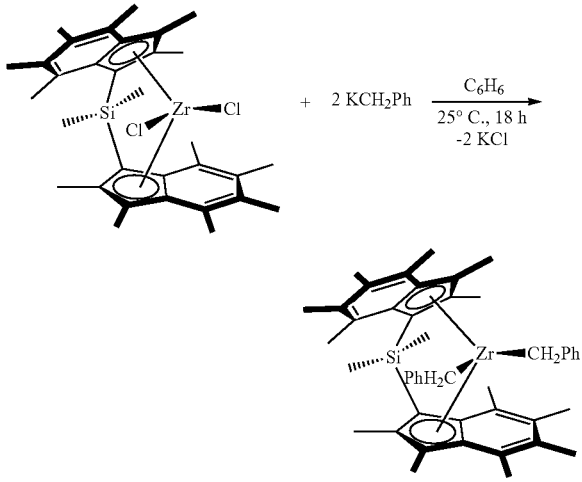

Synthesis of dimethylsiliconbis[1(2,3,4,5,6,7-hexamethylindenyl)]zirconium alkyl, [(SBI*)Zr(CH₂)CH₂SiMe₂]

Using the Si-bridged alkyl indenyl ligand intermediates described above, [(SBI*)Zr(CH₂)CH₂SiMe₂], shown below, was prepared according to the method described in relation to [(SBI*)ZrCl₂] above.

Scheme 3: Synthesis of dimethylsiliconbis[1(2,3,4,5,6,7-hexamethylindenyl)]zirconium alkyl, [(SBI*)Zr(CH₂)CH₂SiMe₂]

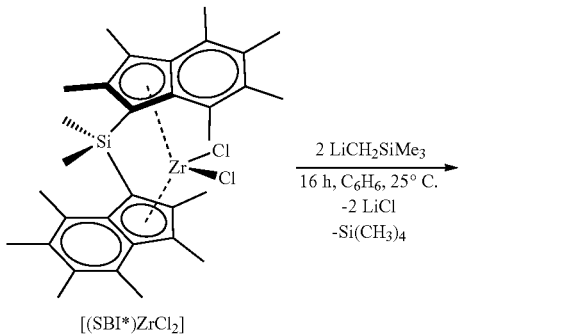

Synthesis of dimethylsiliconbis[1-(2-ethyl-3,4,5,6,7-pentamethylindenyl)]zirconium dichloride, [(SBI*[3-Ethyl])ZrCl₂]

Using the Si-bridged alkyl indenyl ligand intermediates described above, [(SBI*[3-Ethyl])ZrCl₂], shown below, was prepared according to the method described in relation to [(SBI*)ZrCl₂] above.

Scheme 4: Synthesis of dimethylsiliconbis[1(2,3,4,5,6,7-hexamethylindenyl)]zirconium alkyl, [(SBI*,3-Ethyl)ZrCl₂]

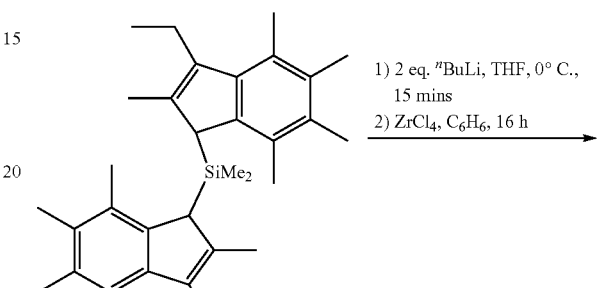

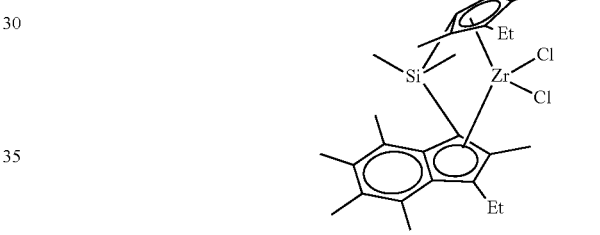

Synthesis of dimethylsiliconbis[1-(2-ethyl-3,4,5,6,7-pentamethylindenyl)]zirconium dibenzyl, [(SBI*[3-Ethyl])Zr(CH₂Ph)₂]

Using the Si-bridged alkyl indenyl ligand intermediates described above, [(SBI*[3-Ethyl])Zr(CH₂Ph)₂], shown below, was prepared according to the method described in relation to [(SBI*)ZrCl₂] above.

Scheme 5: Synthesis of dimethylsiliconbis[1-(2-ethyl-3,4,5,6,7-pentamethylindenyl)]zirconium dibenzyl, [(SBI*3-Ethyl)Zr(CH₂Ph)₂]

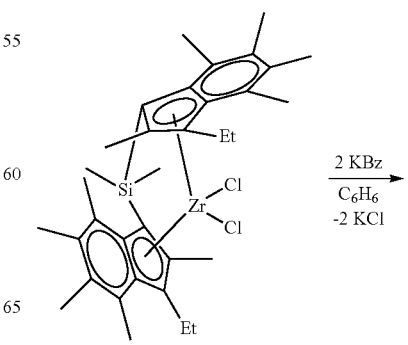

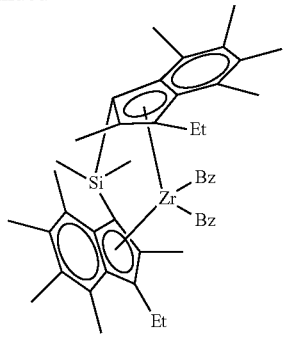

Example 2

Characterisation of Si-Bridged Alkyl Indenyl Zirconocene Complexes

Characterisation of [(SBI*)ZrCl$_2$]

Figure 1:
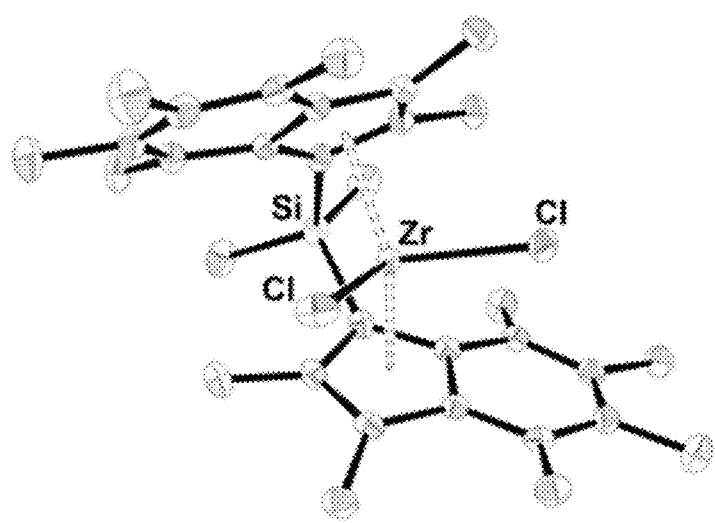
FIG. 1 shows the molecular structure of rac-[(SBI*)ZrCl$_2$] determined by X-ray crystallography.

Single crystals suitable for X-ray crystallography were grown from room temperature benzene solution. The molecular structure of rac-[(SBI*)ZrCl$_2$] is shown in FIG. 1, in which ellipsoids are drawn at 50% probability level. Hydrogen atoms were omitted for clarity. The bond lengths and angles of [(SBI*)ZrCl$_2$] are within the range of the literature.

Figure 2:
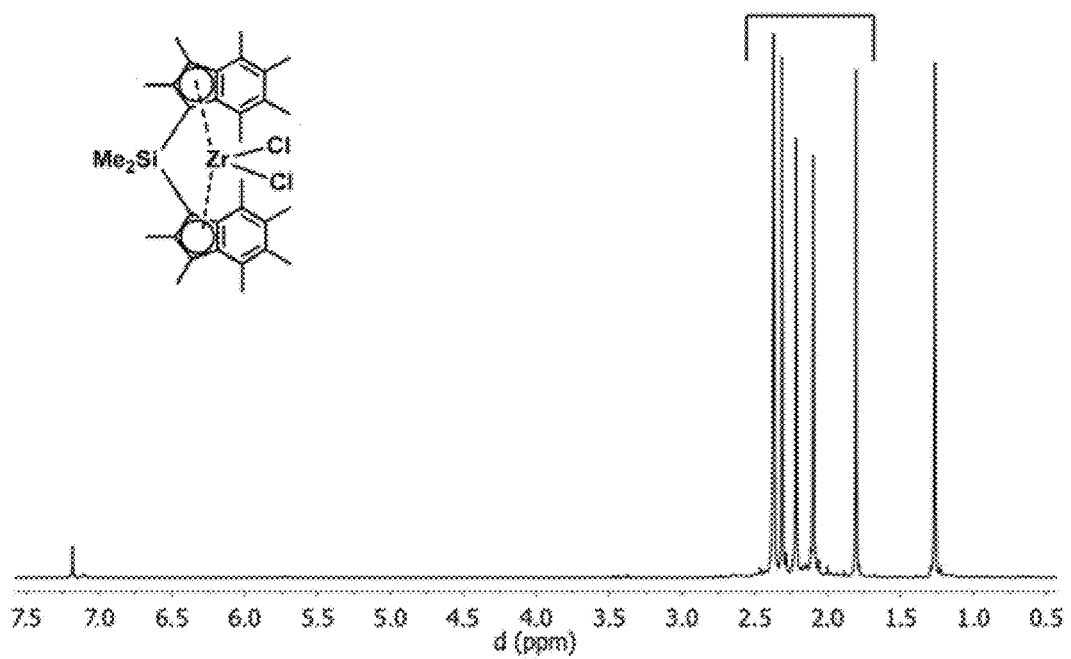
FIG. 2 shows the $^1$H NMR spectroscopy of rac-[(SBI*)ZrCl$_2$] (CDCl$_3$, 23° C., 400 MHz).

The $^1$H NMR spectroscopy of rac-[(SBI*)ZrCl$_2$] is shown FIG. 2. It shows 5 resonances for 36 methyl groups for the ligand around 1.71-2.42 ppm and one resonance for the dimethylsilyl group at 1.28 ppm.

Characterisation of [(SBI*)Zr(CH$_2$Ph)$_2$]

Figure 3:
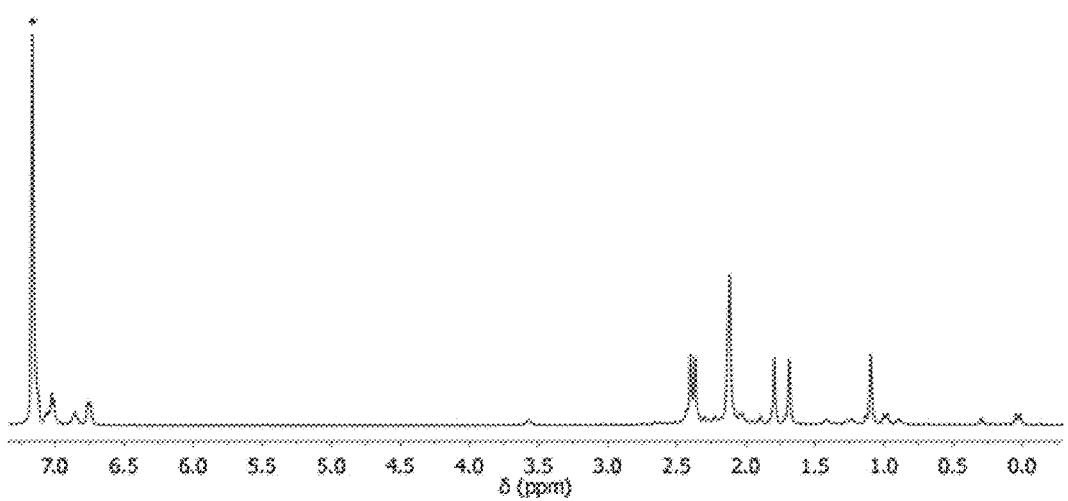
FIG. 3 shows the $^1$H NMR (400 MHz) spectrum of (SBI*)Zr(CH$_2$Ph)$_2$ in benzene-d$_6$. Asterisk marks the residual protio-solvent resonance which is coincident with a multiplet in the aromatic region.

FIG. 3 shows $^1$H NMR (400 MHz) spectrum of (SBI*) Zr(CH$_2$Ph)$_2$ in benzene-d$_6$. Asterisk marks the residual protio-solvent resonance which is coincident with a multiplet in the aromatic region.

$^1$H NMR (400 MHz, C$_6$D$_6$): δ 1.10 (s, 6H, Si-Me), 1.69 (s, 6H, Ar-Me), 1.79 (s, 6H, Ar-Me), 2.11 (s, 12H, Ar-Me), 2.13 (s, 4H, Ph-CH$_2$), 2.37 (s, 6H, Ar-Me), 2.40 (s, 6H, Ar-Me), 6.75 (d, J=7.1 Hz, 4H, o-Ph), 6.85 (t, J=6.5 Hz, 2H, p-Ph), 7.13 (t, J=7.0 Hz, 4H, m-Ph).

$^{13}$C{$^1$H} NMR (400 MHz, C$_6$D$_6$): δ 11.31 (Si-Me), 14.20 (Ar-Me), 15.25 (Ar-Me), 16.41 (Ar-Me), 17.43 (Ar-Me), 17.89 (Ar-Me), 22.00 (Ar-Me), 70.49 (PhCH$_2$), 121.48 (o-Ph), 124.30 (Ar), 125.70 (Ar), 126.81 (p-Ph), 127.94 (Ar), 128.18 (Ar), 128.41 (Ar), 128.57 (m-Ph), 129.33 (Ar), 129.64 (Ar), 131.21 (Ar), 133.72 (Ar), 134.00 (Ar).

IR (KBr) (cm$^{-1}$): 2962, 1544, 1434, 1261, 1093, 1022, 802, 668.

Characterisation of [(SBI*)Zr(CH$_2$)CH$_2$SiMe$_2$]

Figure 4:
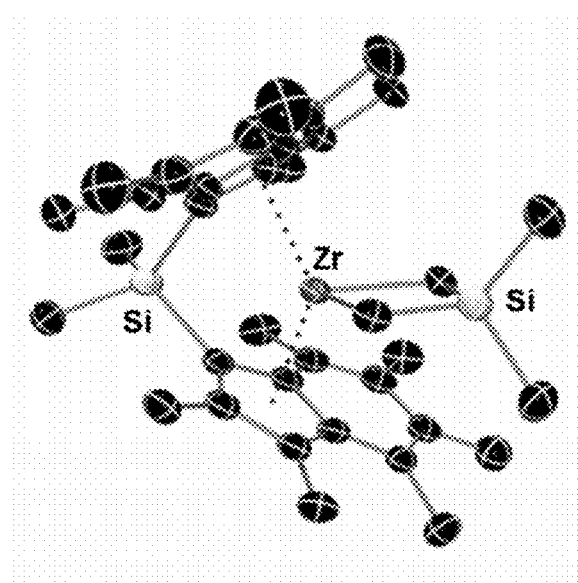
FIG. 4 shows the molecular structure of rac-(SBI*)Zr(CH$_2$)CH$_2$SiMe$_2$, 50% ellipsoids, hydrogen atoms omitted for clarity; grey: carbon, pink: zirconium and green: chloride.

The molecular structure for [(SBI*)Zr(CH$_2$)CH$_2$SiMe$_2$] is shown in FIG. 4, in which ellipsoids are drawn at 50% probability level. Hydrogen atoms were omitted for clarity.

Characterisation of [(SBI*$^{t3-Ethyl}$])ZrCl$_2$]

Figure 5:
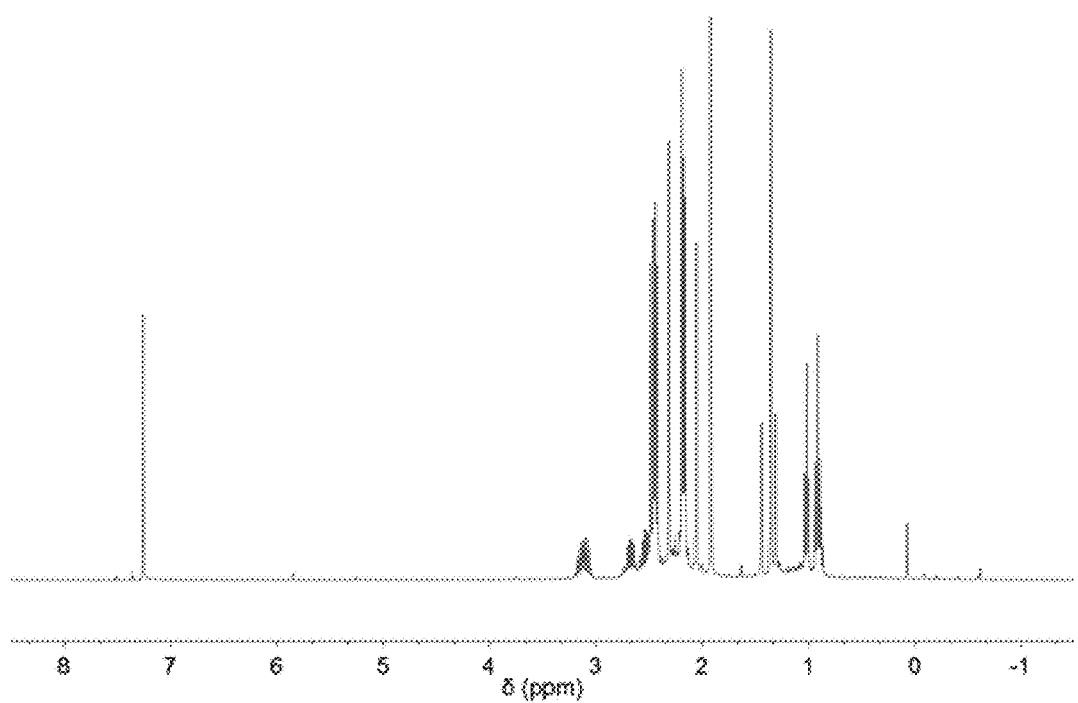
FIG. 5 shows the $^1$H NMR (400 MHz) spectrum of (SBI*$^{\eta3\text{-}Ethyl}$)ZrCl$_2$ in benzene-d$_6$.

FIG. 5 shows $^1$H NMR (400 MHz) spectrum of [(SBI*$^{t3-Ethyl}$])ZrCl$_2$] in benzene-d$_6$.

Figure 6:
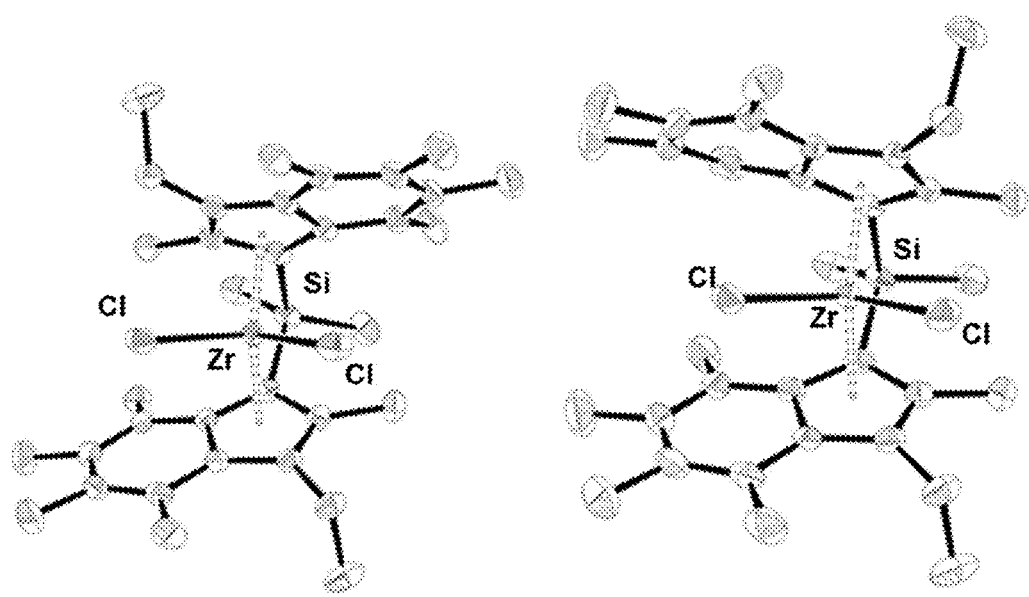
FIG. 6 shows the molecular structure of (SBI*$^{\eta3\text{-}Ethyl}$)ZrCl$_2$ rac- (left) and meso- (right), 50% ellipsoids, hydrogen atoms omitted for clarity; grey: carbon, orange: silicon, pink: zirconium and green: chloride.

The molecular structure for [(SBI*$^{t3-Ethyl}$])ZrCl$_2$] is shown in FIG. 6 (rac: left; meso: right), in which ellipsoids are drawn at 50% probability level. Hydrogen atoms were omitted for clarity.

Characterisation of [(SBI*$^{t3-Ethyl}$])Zr(CH$_2$Ph)$_2$]

Figure 7:
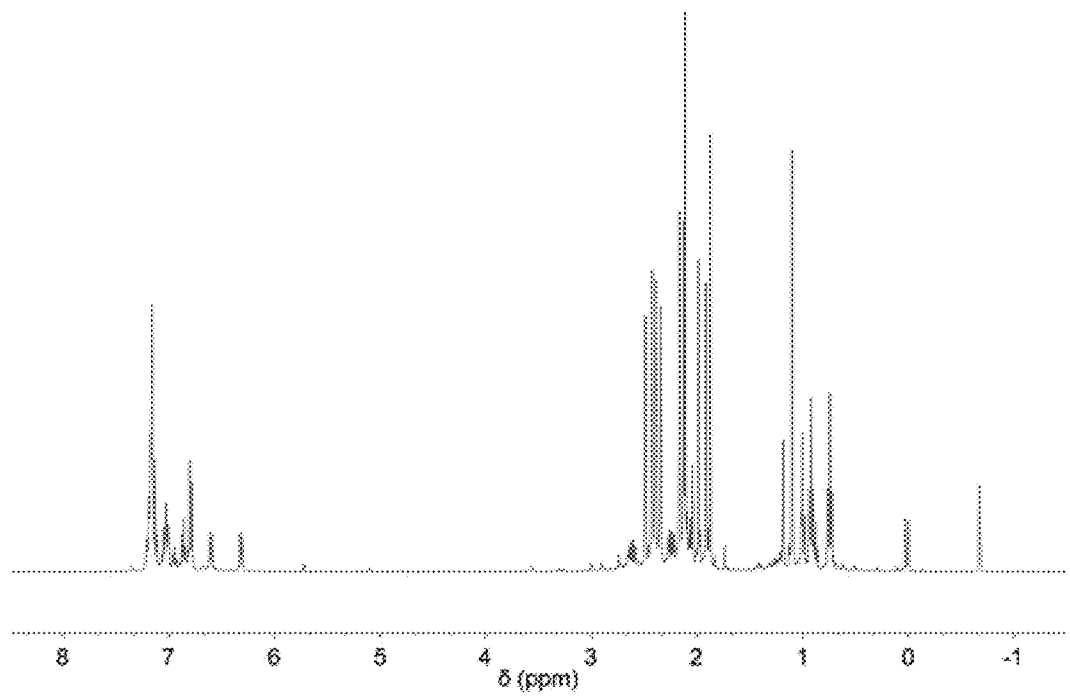
FIG. 7 shows the $^1$H NMR (400 MHz) spectrum of (SBI*$^{\eta3\text{-}Ethyl}$)Zr(CH$_2$Ph)$_2$ in benzene-d$_6$.

FIG. 7 shows $^1$H NMR (400 MHz) spectrum of [(SBI*$^{t3-Ethyl}$])Zr(CH$_2$Ph)$_2$] in benzene-d$_6$.

Figure 8:
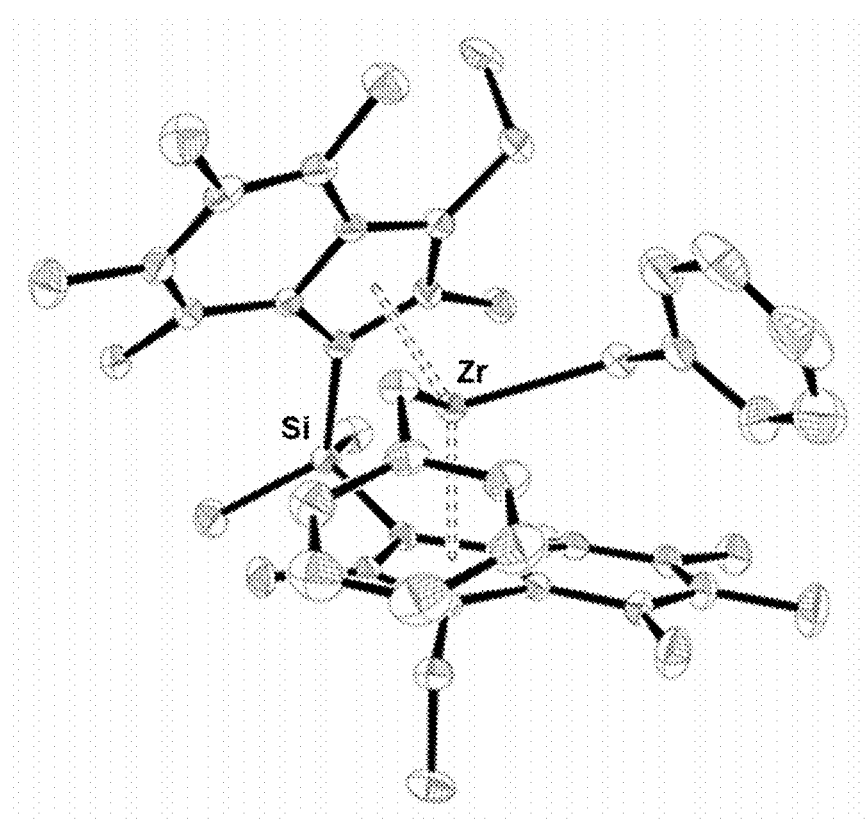
FIG. 8 shows the molecular structure of rac-(SBI*$^{\eta3\text{-}Ethyl}$)Zr(CH$_2$Ph)$_2$, 50% ellipsoids, hydrogen atoms omitted for clarity; grey: carbon, orange: silicon, and pink: zirconium.

The molecular structure for [(SBI*$^{t3-Ethyl}$])Zr(CH$_2$Ph)$_2$] is shown in FIG. 8, in which ellipsoids are drawn at 50% probability level. Hydrogen atoms were omitted for clarity.

Example 3

Synthesis of Activated Solid-Supports (Eg. SSMAO or LDHMAO)

In slurry polymerisation of olefins the molecular procatalysts may be immobilized on an activated support which is insoluble under polymerisation conditions. Suitable solid supports include; methylaluminoxane activated silica (SiO$_2$), solid methylaluminoxane and methylaluminoxane activated AMO-MgAl layered double hydroxide (LDH-MAO) (eg. of an AMO-MgAl is [Mg$_{1-x}$Al$_x$(OH)]$^{x+}$(A$^{n-}$)$_{a/n}$ ▫0.55(H$_2$O)▫0.13 (acetone). (0.1<x>0.9; A=anion eg. CO$_3^{2-}$, SO$_4^{2-}$).

To a Schlenk tube containing a slurry of two equivalents of an amorphous spherical silica or [Mg$_{0.75}$Al$_{0.25}$(OH)$_2$] (SO$_4$)$_{0.125}$▫0.55(H$_2$O)▫0.13(acetone) in toluene (25 ml), a colourless solution of one equivalent of methylaluminoxane in toluene (25 ml) was added swiftly at room temperature. The mixture was heated to 80° C. and left for two hours with occasional swirling. The resulting suspension was then left to cool down to room temperature and the toluene solvent was carefully filtered and removed in vacuo to obtain methylaluminoxane activated silica (SSMAO) or methylaluminoxane activated AMO-MgAl layered double hydroxide (LDHMAO) as a white, free-flowing powders in quantitative yield (3.14 g).

Example 4

Synthesis of Solid-Supported [(SBI*)ZrCl$_2$] Catalysts

To a Schlenk tube containing a slurry of SSMAO, LDH-MAO or Solid MAO (1.00 g) in toluene (25 ml), a solution of an appropriate amount of an orange solution of [(SBI*)ZrCl$_2$] in toluene (25 ml) was added swiftly at room temperature. The mixture was heated to 60° C. and left, with occasional swirling, for two hours during which time the solution turned colourless and the solid colourised purple. The resulting suspension was then left to cool down to room temperature and the toluene solvent was carefully filtered and removed in vacuo to obtain solid-supported [(SBI*) ZrCl$_2$] catalyst as a light purple, free-flowing powder.

Figure 9:
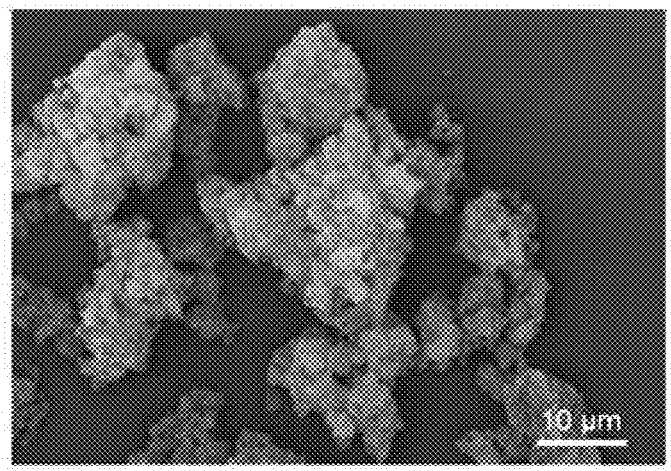
FIG. 9 shows scanning electron microscopy images at 500 and 5000× magnification. a) AMO-MgAl—SO$_4$ LDH; b) AMO-MgAl—SO$_4$ LDHMAO; c) AMO-MgAl—SO$_4$ LDH-MAO-(SBI*)ZrCl$_2$.
Figure 9:
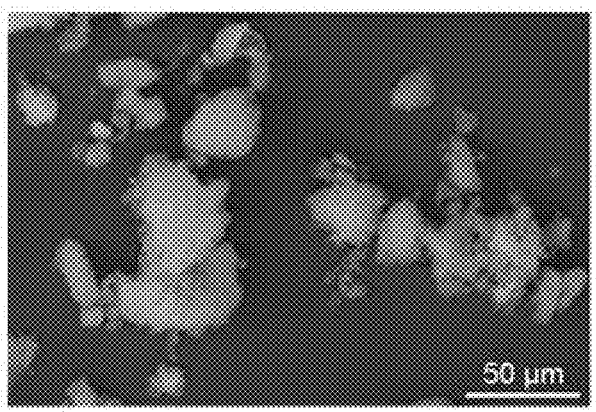
Figure 9:
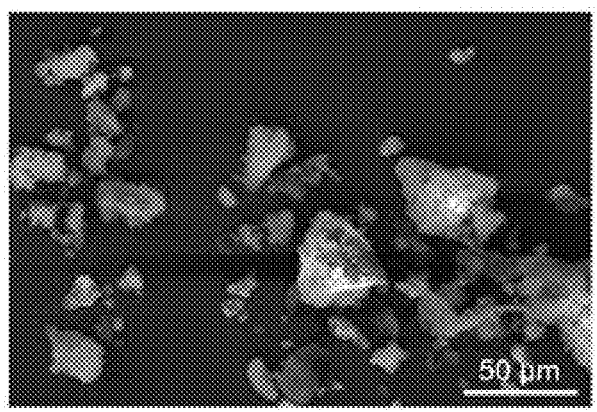

FIG. 9 shows scanning electron microscopy images at 500 and 5000× magnification. a) AMO-MgAl—SO$_4$ LDH; b) AMO-MgAl—SO$_4$ LDHMAO; c) AMO-MgAl—SO$_4$ LDH-MAO-(SBI*)ZrCl$_2$. FIG. 9 clearly reveals two points; small particle size of AMO-LDHs and the consistency of their morphology under the immobilisation process. Image a) illustrates the small diameters of the individual particles, which are poorly resolved even under 5000× magnification, and a high surface area was anticipated. It is also noteworthy that there is a significant degree of aggregation of the smaller particles. Images b) and c) display the fine detail which appears unaffected by the reaction with MAO or the complex -(SBI*)ZrCl$_2$ as well as the aggregation noted above.

LDHMAO-(SBI*)ZrCl$_2$ $^{13}$C CPMAS NMR: δ −9.32 (AlOMe), 12.87 (SiMe$_2$), 22.44 (Ar-Me), 24.57 (Ar-Me), 29.54 (Ar-Me), 31.10 (Ar-Me), 74.97 (Cp), 128.39 (Ar).
$^{27}$Al CPMAS NMR: δ −527, −28, 470.

LDHMAO-(SBI*)ZrCl$_2$ $\lambda_{max}$=395 nm.

Figure 10:
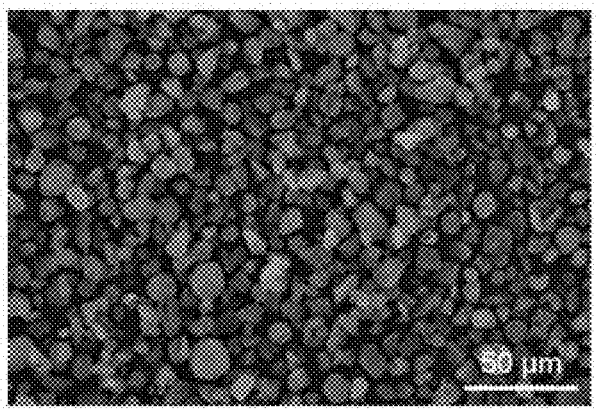
FIG. 10 shows scanning electron microscopy images at 500× magnification. a) amorphous SiO$_2$ (Grace); b) SSMAO; c) SSMAO-(SBI*)ZrCl$_2$.
Figure 10:
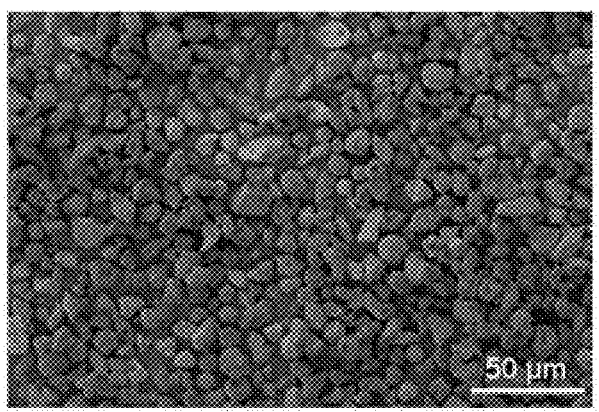
Figure 10:
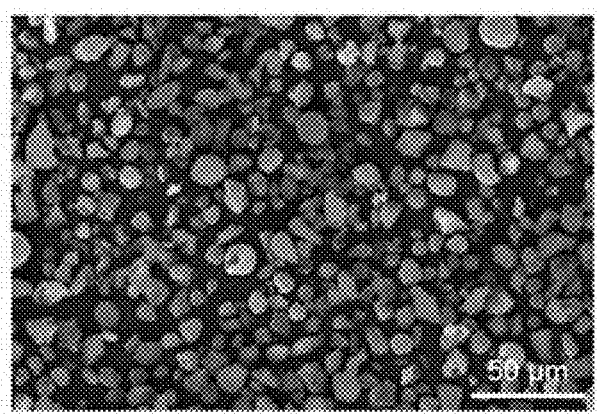

FIG. 10 shows scanning electron microscopy images at 500× magnification. a) amorphous SiO$_2$ (Grace); b) SSMAO; c) SSMAO-(SBI*)ZrCl$_2$. FIG. 10 illustrates a dramatically different particle morphology from LDH. The silica, supplied by Grace, is much more uniform in shape and size with no aggregation. The particles are not spherical but granular with an average size of approximately 10 μm. They do not change in either shape or dimension on reaction with MAO, nor on the immobilisation of (SBI*)ZrCl$_2$. It can be seen that no further aggregation has occurred, justifying the omission of stirrer bars during the supporting procedure.

SSMAO-(SBI*)ZrCl$_2$ $^{13}$C CPMAS NMR: δ −9.03 (AlOMe).
$^{27}$Al CPMAS NMR: δ −309, −113, 3, 182, 336.
$^{29}$Si CP SSMAO-EBI*ZrCl$_2$: $\lambda_{max}$=390 nm.

SSMAO-(SBI*)ZrCl$_2$ $\lambda_{max}$=390 nm.

Example 5

Ethylene Polymerization Studies

Unsupported [(SBI*)ZrCl$_2$]

Figure 11:
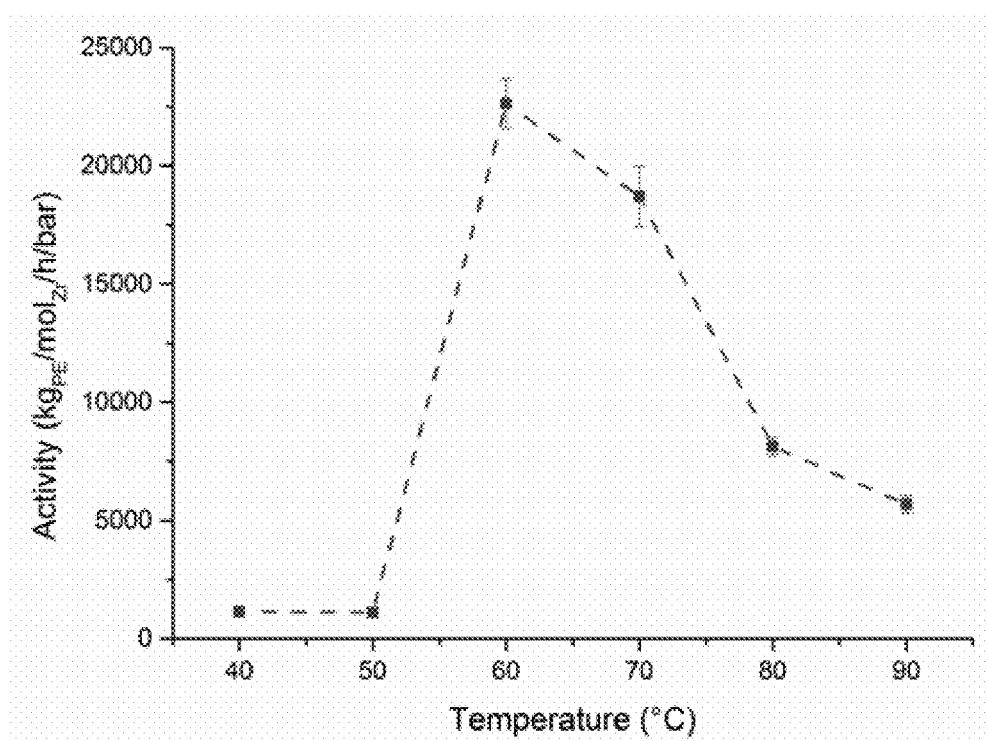
FIG. 11 shows a graph demonstrating the ethylene polymerisation activity dependence of rac-(SBI*)ZrCl$_2$ on temperature. MAO (2000:1); 2 bar ethylene; 0.2 mg catalyst loading; 50 ml hexane; timed until cessation of stirring.

Unsupported rac-SBI*ZrCl$_2$ was used to catalyse the polymerisation of ethylene at a range of temperatures from 40-90° C. using methylaluminoxane (MAO) as the co-catalyst and scavenger (FIG. 11). The most striking feature of the temperature profile for rac-SBI*ZrCl$_2$ in solution is the activity achieved at 60° C. (22,622 kg$_{PE}$/mol$_{Zr}$/h/bar) which compares well with some of the highest reported values in the literature. Another interesting feature is the sharp increase in activity seen between 50 (1,123 kg$_{PE}$/mol$_{Zr}$/h/bar) and 60° C. (22,622 kg$_{PE}$/mol$_{Zr}$/h/bar). The weight average molecular weight, M$_w$, of the resultant polymer was seen to peak at 70° C. (261,337 daltons), up from 213,927 daltons at the activity peak (60° C.). A drop-off is also noted at 80° C. to c. 200,000 daltons. The molecular weight distribution (MWD), measured by the polydispersity index (PDI), was also recorded and was found to increase with increasing temperature from 2.32 (60° C.) to 2.99 (80° C.).

Figure 12:
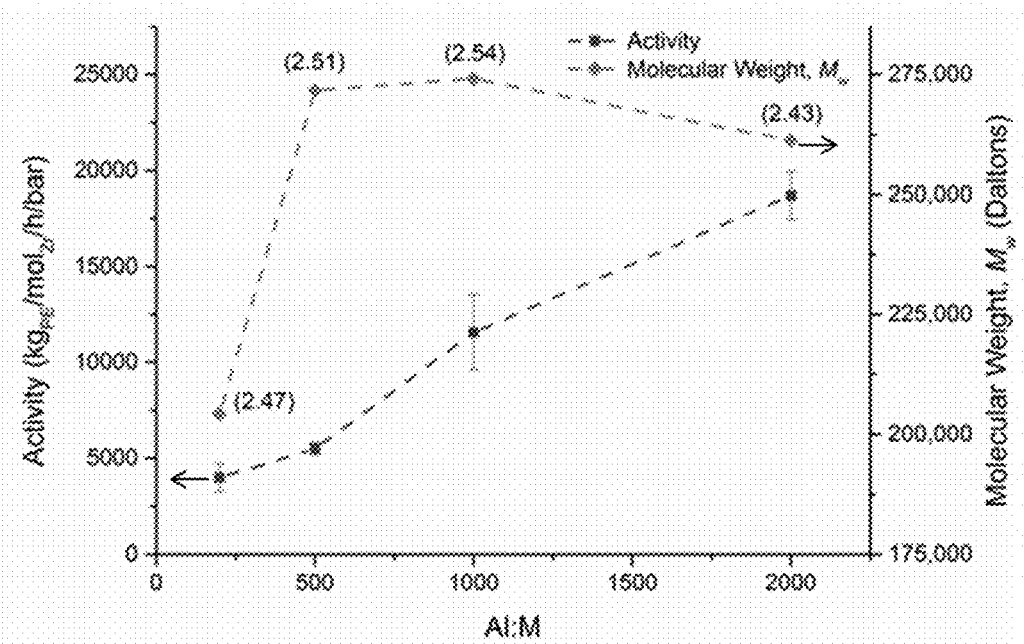
FIG. 12 shows a graph demonstrating the dependence of activity and molecular weight, M$_w$, for rac-(SBI*)ZrCl$_2$ on the Al:Zr co-catalyst (MAO) ratio. PDIs are given in parentheses. 70° C.; 2 bar ethylene; 0.2 mg catalyst loading; 50 ml hexane; timed until cessation of stirring.

A study was undertaken with rac-(SBI*)ZrCl$_2$ to test the effect that the Al:Zr ratio has on activity (FIG. 12) and the value for M$_w$ and M$_n$, the number average molecular weight, were measured in each case. The polymerisation runs were carried out at 70° C. for ease of comparison since most of the catalysts tested are at or near their optima at this temperature. A very strong dependence of the activity on the Al:Zr ratio was noted, with a linear regression of R$^2$=0.9862 calculated. The activity at 2000:1 (18,703 kg$_{PE}$/mol$_{Zr}$/h/bar) is more than four greater than that at 200:1 (3,996 kg$_{PE}$/mol$_{Zr}$/h/bar). The behaviour of M$_w$ is quite unusual, however. At an Al:Zr ratio of 200, it is recorded as 204,374 daltons rising quickly to 271,713 daltons at a ratio of 500 and plateauing on further increases.

[(SBI*)ZrCl$_2$] Supported on SSMAO and LDHMAO

The solid-supported [(SBI*)ZrCl$_2$] catalysts were tested for their ethylene polymerisation activity under slurry conditions in the presence of tri(isobutyl)aluminium (TIBA), an aluminium-based scavenger. The reactions were performed under 2 bar of ethylene in a 200 ml ampoule, with 10 mg of the catalyst suspended in 50 ml of hexane. The reactions were run for 60 minutes at 60° C. and 80° C. controlled by heating in an oil bath. The resulting polyethylene was immediately filtered under vacuum through a dry sintered glass frit. The polyethylene product was then washed with pentane (2×50 ml) and then dried on the frit for at least one hour. The tests were carried out at least twice for each individual set of polymerisation conditions.

As shown in Table 1 below, preliminary results demonstrated that ethylene polymerisation using SSMAO-[(SBI*)ZrCl$_2$] had an activity of 1,173 and 2,160 kg$_{PE}$/mol$_{Zr\ complex}$/h at 80 and 60° C. respectively. However, the activity is five times higher at 60° C. using MgAl—SO$_4$/MAO as a support (activity of 11,761 kg$_{PE}$/mol$_{Zr\ complex}$/h). The polydispersity is low (M$_w$/M$_n$ of 2.40) and relatively high molecular weight M$_w$ of 276,905 g/mol.

TABLE 1

Ethylene polymerisation activity, PE molecular weight and polydispersity for [(SBI*)ZrCl$_2$] supported on MAO activated silica and MAO activated AMO-layered double hydroxide (MAOLDH)

| Support | T (° C.) | Average activity (kg$_{PE}$/mol$_{Zr\ complex}$/h) | M$_w$ (g/mol) | M$_w$/M$_n$ |
|---|---|---|---|---|
| SSMAO$^a$ | 80 | 1,173 | — | — |
| SSMAO$^a$ | 60 | 2,160 | — | — |
| MgAl—SO$_4$/MAO$^b$ | 60 | 11,761 | 276,905 | 2.40 |

$^a$SSMAO is MAO activated spherical amorphous silica.
$^b$MgAl—SO$_4$/MAO is an MAO activated AMO-LDH.
MgAl—SO$_4$ has the formula [Mg$_{0.75}$Al$_{0.25}$(OH)$_2$](SO$_4$)$_{0.125}$☐0.55(H$_2$O)☐0.13(acetone).

As shown in Table 2 below, ethylene polymerisation using MgAl—SO$_4$/MAO as a support demonstrated that MgAl—SO$_4$/MAO-[(SBI*)ZrCl$_2$] had an activity of 11,761 kg$_{PE}$/mol$_{Zr\ complex}$/h at 60° C., five and six times higher than ethylene-bridged analogues, [(EBI*)ZrCl$_2$] and [(EBI)ZrCl$_2$] (structures shown below), respectively (activity of 2,263 and 1,862 kg$_{PE}$/mol$_{Zr\ complex}$/h respectively). Furthermore, the molecular weight for [(SBI*)ZrCl$_2$] is higher (M$_w$ of 276,905 g/mol) than the two ethylene-bridged complexes (M$_w$ of 251,512 g/mol for [(EBI*)ZrCl$_2$] and M$_w$ of 213,804 g/mol for [(EBI)ZrCl$_2$]). The polydispersity is far lower for the permethylated complexes (M$_w$/M$_n$<2.40) in comparison with the non-permethylated version (M$_w$/M$_n$ of 3.76).

TABLE 2

Ethylene polymerisation activity, PE molecular weight and polydispersity for bridged indenyl complexes supported on MgAl—SO$_4$/MAO; which is a MAO activated AMO-LDH (LDHMAO)

| Support | T (° C.) | Average activity (kg$_{PE}$/mol$_{Zr\ complex}$/h) | M$_w$ (g/mol) | M$_w$/M$_n$ |
|---|---|---|---|---|
| [(EBI)ZrCl$_2$] | 60 | 1,862 | 213,804 | 3.76 |
| [(EBI*)ZrCl$_2$] | 60 | 2,263 | 251,512 | 2.36 |
| [(SBI*)ZrCl$_2$] | 60 | 11,761 | 276,905 | 2.40 |

MgAl—SO$_4$/MAO is an MAO activated AMO-LDH. The AMO-LDH (MgAl—SO$_4$) has the formula [Mg$_{0.75}$Al$_{0.25}$(OH)$_2$](SO$_4$)$_{0.125}$□0.55(H$_2$O)□0.13(acetone).

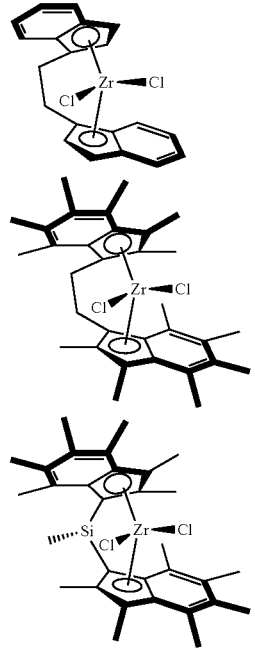

[(EBI)ZrCl$_2$], [(EBI*)ZrCl$_2$] and [(SBI*)ZrCl$_2$]

Figure 13:
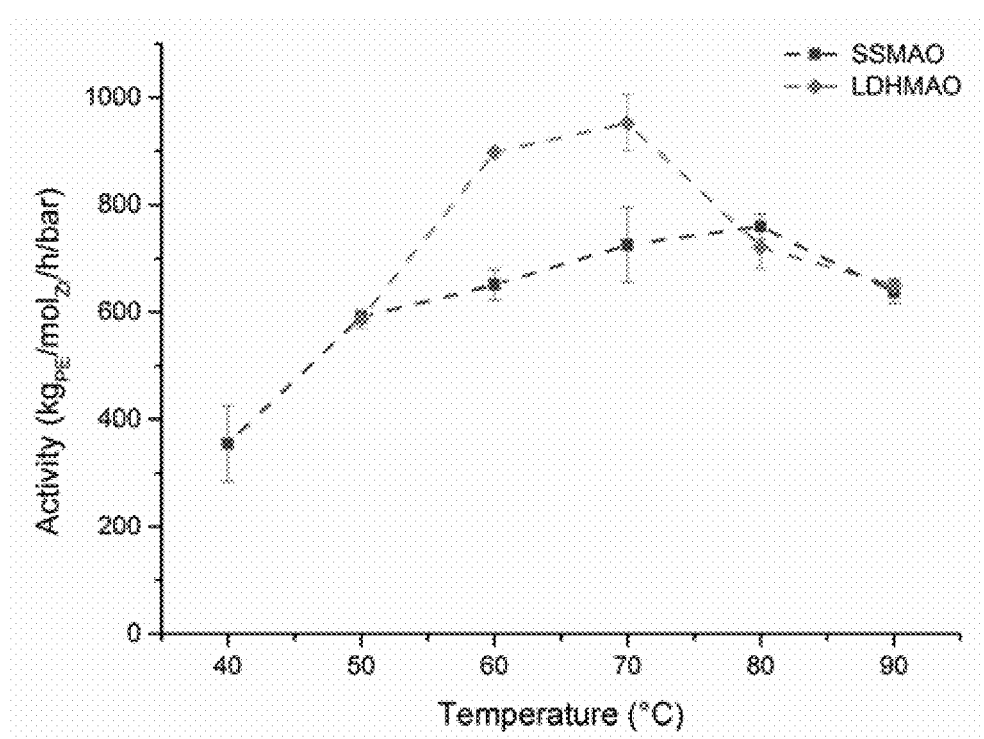
FIG. 13 shows a graph demonstrating the ethylene polymerisation activity dependence of rac-(SBI*)ZrCl$_2$ on temperature, supported on SSMAO (200:1 loading) and LDHMAO (300:1 loading). TIBA co-catalyst; 2 bar ethylene; 10 mg catalyst; 50 ml hexane; 30 minutes.

FIG. 13 is a graph showing the ethylene polymerisation activity dependence of rac-(SBI*)ZrCl$_2$ on temperature, supported on SSMAO (200:1 loading) and LDHMAO (300:1 loading). It is clear that the LDH supported catalyst displays a higher activity (953 kg$_{PE}$/mol$_{Zr}$/h/bar at 70° C.) than that achieved by its silica counterpart (759 kg$_{PE}$/mol$_{Zr}$/h/bar at 80° C.). The trends identified are similar with an optimum seen in both cases and the activity diminishing on either heating or cooling.

FIG. 14 is a graph showing the dependence of activity and M$_w$ on temperature for rac-(SBI*)ZrCl$_2$ supported on SSMAO (200:1 loading). PDIs are given in parentheses. FIG. 14 shows that the molecular weights obtained using rac-(SBI*)ZrCl$_2$ supported on SSMAO are higher (258,536 daltons; 60° C.) than those obtained using rac-EBI*ZrCl$_2$ (202,746 daltons; 60° C.). The molecular weight trend for rac-(SBI*)ZrCl$_2$ on SSMAO sees a decline in molecular weight with increasing temperature.

FIG. 15 is a graph showing the dependence of activity and M$_w$ on length or run for rac-(SBI*)ZrCl$_2$ supported on SSMAO (200:1 loading). PDIs are given in parentheses. As with rac-EBI*ZrCl$_2$, rac-(SBI*)ZrCl$_2$ on SSMAO was tested to see the effect of increasing the residence time on the activity and M$_w$. The activity trends in both cases are very similar, with the rate decreasing on increased length of run. However, the relative decrease in activity is not as severe for rac-(SBI*)ZrCl$_2$: a reduction of 1.4× as opposed to 2.1×. The value of M$_w$ drops off at two hours which is not seen for rac-EBI*ZrCl$_2$ on SSMAO.

[(SBI*)ZrCl$_2$] Supported on Solid MAO

Ethylene polymerisation studies were also performed using [(SBI*)ZrCl$_2$] supported on Solid MAO (the solid MAO support is as described in US2013/0059990 and obtainable from Tosoh Finechem Corporation, Japan).

FIG. 16 is a graph showing the dependence of activity and M$_w$ on temperature for rac-(SBI*)ZrCl$_2$ supported on Solid MAO (300:1 loading). PDIs are given in parentheses. FIG. 17 is a graph showing the ethylene polymerisation activity dependence on temperature for rac-EBI*ZrCl$_2$ and rac-(SBI*)ZrCl$_2$ supported on Solid MAO (200:1 loading for rac-(EBI*)ZrCl$_2$; 300:1 loading for rac-(SBI*)ZrCl$_2$). FIGS. 16 and 17 focus on rac-(SBI*)ZrCl$_2$ immobilised on solid MAO—FIG. 16 displaying both activity and molecular weight data with FIG. 17 offering a comparison of the activity with rac-EBI*ZrCl$_2$. Clearly the activity of rac-(SBI*)ZrCl$_2$ on Solid MAO is very high, bordering on exceptional in comparison with literature, and peaking at 70° C. (7,760 kg$_{PE}$/mol$_{Zr}$/h/bar). As outlined above, the best values reported hitherto are Cp$_2$ZrCl$_2$, EBTHIZrCl$_2$, and Cp'$_2$ZrCl$_2$ which show activities of 5,400, 4,320, and 9,180 kg$_{PE}$/mol$_{Zr}$/h/bar (all at 60° C.) respectively; all of these bar the dimethylzirconocene dichloride are improved upon by rac-(SBI*)ZrCl$_2$. In addition, the high activities reported are remarkably temperature stable, maintaining ethylene polymerisation activities in excess of 6,000 kg$_{PE}$/mol$_{Zr}$/h/bar, and outperforming rac-EBI*ZrCl$_2$ on Solid MAO, from 50 to 70° C. At either end of the temperature spectrum measured, the activity is seen to dip but still remains as one of the highest activity supported catalysts known in the academic literature.

It is clear from FIG. 16 that M$_w$ is also high and a value of 288,557 daltons is recorded at 40° C. This decreases rapidly on heating, falling below 150,000 daltons by 90° C. The PDIs narrow in the middle of the temperature range as previously described.

The synergy of complex and support is clearly demonstrated here as the activities reported for rac-(SBI*)ZrCl$_2$ on SSMAO and LDHMAO clearly trail those for rac-EBI*ZrCl$_2$. However, on changing the immobilisation surface to Solid MAO, rac-(SBI*)ZrCl$_2$ experiences a much more marked improvement than rac-EBI*ZrCl$_2$. There is a ten-fold increase in performance from SSMAO to Solid MAO for rac-(SBI*)ZrCl$_2$ compared to just 2.5 times for rac-EBI*ZrCl$_2$. While this increase is remarkable, the drop from the reported value of 22,622 kg$_{PE}$/mol$_{Zr}$/h/bar in solution is also very significant.

In contrast to the large activity variation observed across different media for rac-(SBI*)ZrCl$_2$, the molecular weight and PDI are comparatively constant (FIG. 18). The well-ordered layered structure of LDHMAO gives rise to high molecular weight polymer and a narrow PDI (297,583 daltons and 2.74). The values for the solution polymerisation and the SSMAO immobilised run are intermediate.

rac-(SBI*$^{t3\text{-}ethyl}$)ZrCl$_2$ Supported on Solid MAO

FIGS. 19 and 20 show the polymerisation of ethylene using Solid MAO supported rac-(SBI*$^{t3\text{-}ethyl}$)ZrCl$_2$ as a function of time and temperature. When comparing these results with earlier data, it is clear that rac-(SBI*)ZrCl$_2$ is generally 1.5 to 2 times faster than rac-(SBI*$^{t3-ethyl}$)ZrCl$_2$ over time and temperature.

Unsupported rac-(SBI*$^{t3-ethyl}$)ZrCl$_2$

FIG. 21 shows the solution polymerisation using unsupported rac-(SBI*$^{t3-ethyl}$)ZrCl$_2$ with activity around 11 000 kg$_{PE}$/mol$_{Zr}$/h/bar, which is close to four times higher than when supported on Solid MAO.

Example 6

Ethylene and α-Olefin Polymerization Studies

In addition to the homo-polymerisation of ethylene, co-polymerisation with 1-hexene was carried out to test the co-monomer incorporation (FIG. 22). It shows a clear "co-monomer effect", enhanced activity with respect to the homo-polymerisation up to 5% (v/v) loading of 1-hexene.

The $^{13}$C NMR spectroscopy data for the resulting polymer the rate of 1-hexene incorporation was impressive (Table 3). rac-SBI*ZrCl$_2$ was able to incorporate effectively double the proportion of co-monomer: 0.4 and 0.8 mol % at 5 and 10% concentrations of 1-hexene respectively. As well as improved levels of 1-hexene incorporation, rac-SBI*ZrCl$_2$ maintains high molecular weights on addition of co-monomer at all concentrations (Table 4).

TABLE 3

1-hexene incorporation (mol %) into the final polymer as determined by $^{13}$C NMR spectroscopy at different concentrations of co-monomer.

| Catalyst | 5% (v/v) 1-hexene 1-hexene incorporation (mol %) | 10% (v/v) 1-hexene 1-hexene incorporation (mol %) |
|---|---|---|
| rac-SBI * ZrCl$_2$ | 0.4 | 0.8 |

Polymerisation conditions: supported on Solid MAO (300:1); 70° C.; 5 ml heptane; 15 µmol AlEt$_3$; 8.274 bar ethylene; 0.1-0.5 mg catalyst.

TABLE 4

M$_w$ (daltons) and PDI data for the final polymer as determined by GPC at different concentrations of 1-hexene.

| | 2% (v/v) 1-hexene | | 5% (v/v) 1-hexene | | 10% (v/v) 1-hexene | |
|---|---|---|---|---|---|---|
| Catalyst | M$_w$ | PDI | M$_w$ | PDI | M$_w$ | PDI |
| rac-SBI * ZrCl$_2$ | 384,000 | 4.4 | 302,000 | 3.3 | 244,000 | 2.8 |
| rac-SBI * ZrCl$_2$ | 384,000 | 4.4 | 302,000 | 3.3 | 244,000 | 2.8 |

Polymerisation conditions: supported on Solid MAO (300:1); 70° C.; 5 ml heptane; 15 µmol AlEt$_3$; 8.274 bar ethylene; 0.1-0.5 mg catalyst Further to the characterisation by $^{13}$C NMR spectroscopy, the co-polymer was analysed by crystallisation elution fractionation (CEF). This corroborated the 1-hexene incorporation data as well as analysing the amorphous fractions (AF) and temperatures of melting (Table 5).

TABLE 5

Temperature at maximum elution (° C.) and amorphous fraction (%) data for the final polymer as determined by CEF at different concentrations of 1-hexene.

| | 2% (v/v) 1-hexene | | 5% (v/v) 1-hexene | | 10% (v/v) 1-hexene | |
|---|---|---|---|---|---|---|
| Catalyst | T$_{el.\ max.}$ (° C.) | AF (%) | T$_{el.\ max.}$ (° C.) | AF (%) | T$_{el.\ max.}$ (° C.) | AF (%) |
| rac-SBI*ZrCl$_2$ | 111.3 | — | 110.4 | — | 109.2 | — |

Polymerisation conditions: supported on Solid MAO (300:1); 70° C.; 5 ml heptane; 15 µmol AlEt$_3$; 8.274 bar ethylene; 0.1-0.5 mg catalyst.

The data for the temperature at maximum elution (T$_{el.\ max.}$) fits very well with the 1-hexene incorporation data: T$_{el.\ max.}$ decreases as the proportion of 1-hexene in the co-polymer rises. Poly(1-hexene) has a much lower glass transition temperature (T$_g$) and melting temperature than PE, and this is reflected in the reduction of T$_{el.\ max.}$ with increasing 1-hexene concentration. At 0.8% incorporation, the temperature of elution has decreased to 109.2° C. (rac-SBI*ZrCl$_2$ at 10% 1-hexene). Viscosity measurements were also recorded and these were found to be in good agreement with the molecular weight data obtained by GPC.

While specific embodiments of the invention have been described herein for the purpose of reference and illustration, various modifications will be apparent to a person skilled in the art without departing from the scope of the invention as defined by the appended claims.

The invention claimed is:

1. A compound of the formula I shown below:

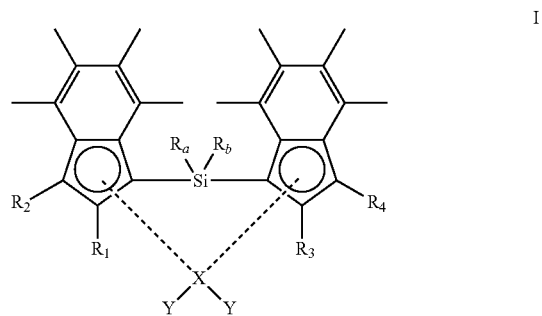

I wherein:

R$_1$ and R$_3$ are methyl;

R$^2$ and R$^4$ are independently methyl or ethyl;

R$_a$ and R$_b$ are independently (1-4C)alkyl;

X is zirconium; and each Y group is independently halo.

2. The compound according to claim 1, wherein R$_2$ and R$_4$ are both methyl.

3. The compound according to claim 1, wherein Y is chloro.

4. The compound according to claim 3, wherein $R_a$ and $R_b$ are each independently selected from the group consisting of methyl and propyl.

5. The compound according to claim 1, where the compound has the structural formula:

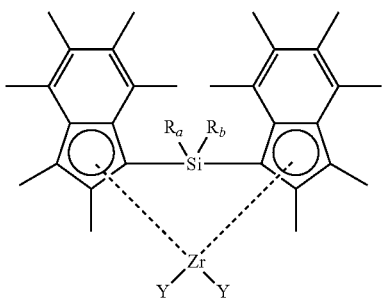

wherein:

$R_a$ and $R_b$ are each independently selected from the group consisting of methyl and propyl; and Y is chloro.

6. A compound of the structural formula:

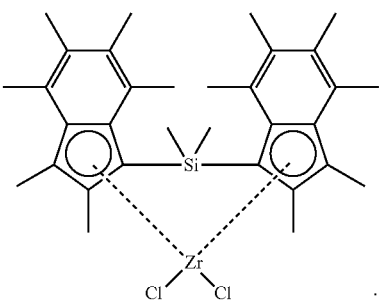

7. A composition comprising a compound of formula I as defined in claim 1, and an activator.

8. The composition of claim 7, wherein the activator is solid MAO and the compound of formula I is supported thereon.

9. A process for forming a polyethylene which comprises reacting olefin monomers in the presence of (i) a compound of formula I as defined in claim 1, and (ii) an activator.

10. The process according to claim 9, wherein the activator comprises an aluminoxane, tri(isobutyl)aluminium (TIBA) or triethylaluminium (TEA).

11. The process according to claim 9, wherein the activator is provided as an activated support.

12. The process according to claim 11, wherein the compound of formula I is supported on the activated support.

13. The process according to claim 11, wherein the activated support is methylaluminoxane activated silica or methylaluminoxane activated AMO-MgAl layered double hydroxide.

14. The process according to claim 11, wherein the activated support is solid methylaluminoxane.

* * * * *